United States Patent
Rentschler et al.

(10) Patent No.: US 12,369,997 B2
(45) Date of Patent: Jul. 29, 2025

(54) AUTONOMOUS NAVIGATION AND INTERVENTION IN THE GASTROINTESTINAL TRACT

(71) Applicant: The Regents of the University of Colorado, Denver, CO (US)

(72) Inventors: Mark E. Rentschler, Boulder, CO (US); Gregory Formosa, Boulder, CO (US); Joseph M. Prendergast, Boulder, CO (US); Mitchell J. Fulton, Boulder, CO (US)

(73) Assignee: The Regents of the University of Colorado, a body corporate

( * ) Notice: Subject to any disclaimer, the term of this patent is extended or adjusted under 35 U.S.C. 154(b) by 594 days.

(21) Appl. No.: 17/567,665

(22) Filed: Jan. 3, 2022

(65) Prior Publication Data

US 2022/0211449 A1     Jul. 7, 2022

Related U.S. Application Data

(60) Provisional application No. 63/133,535, filed on Jan. 4, 2021.

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00006* (2013.01); *A61B 1/000094* (2022.02);
(Continued)

(58) Field of Classification Search
CPC .......... A61B 1/00006; A61B 1/000094; A61B 1/00087; A61B 1/041; A61B 1/31;
(Continued)

(56) References Cited

U.S. PATENT DOCUMENTS

| 2003/0076411 A1* | 4/2003 | Iida | H04N 7/183 |
| | | | 348/E7.087 |
| 2005/0157168 A1* | 7/2005 | Kaneko | A61B 1/00059 |
| | | | 348/72 |

(Continued)

OTHER PUBLICATIONS

Detection and Measurement of Arc of Lumen Calcification from Intravascular Ultrasound using Harris Corner Detection (Year: 2012).*

(Continued)

*Primary Examiner* — Anh Tuan T Nguyen
*Assistant Examiner* — Shankar Raj Ghimire
(74) *Attorney, Agent, or Firm* — Polsinelli PC

(57) ABSTRACT

Implementations include herein are visual navigation strategies and systems for lumen center tracking comprising a high-level state machine for gross (i.e., left/right/center) region prediction and curvature estimation and multiple state-dependent controllers for center tracking, wall-avoidance and curve following. This structure allows a navigation system to navigate even under the presence of significant occlusion that occurs during turn navigation and to robustly recover from mistakes and disturbances that may occur while attempting to track the lumen center. This system comprises a high-level state machine for gross region prediction, a turn estimator for anticipating sharp turns, and several lower level controllers for heading adjustment.

6 Claims, 19 Drawing Sheets

(51) Int. Cl.

| | |
|---|---|
| *A61B 1/04* | (2006.01) |
| *A61B 1/31* | (2006.01) |
| *A61B 5/06* | (2006.01) |
| *A61B 10/04* | (2006.01) |
| *A61B 10/06* | (2006.01) |
| *A61B 34/20* | (2016.01) |
| *G06T 7/11* | (2017.01) |
| *G06T 7/66* | (2017.01) |
| *G06T 7/70* | (2017.01) |
| *G16H 20/40* | (2018.01) |
| *G16H 30/40* | (2018.01) |
| *G16H 40/63* | (2018.01) |
| *A61M 25/01* | (2006.01) |

(52) U.S. Cl.
CPC .......... *A61B 1/00087* (2013.01); *A61B 1/041* (2013.01); *A61B 1/31* (2013.01); *A61B 5/062* (2013.01); *A61B 10/04* (2013.01); *A61B 10/06* (2013.01); *G06T 7/11* (2017.01); *G06T 7/66* (2017.01); *G06T 7/70* (2017.01); *G16H 20/40* (2018.01); *G16H 30/40* (2018.01); *G16H 40/63* (2018.01); *A61B 2034/2065* (2016.02); *A61B 2034/301* (2016.02); *A61M 25/0113* (2013.01); *G06T 2207/10016* (2013.01); *G06T 2207/10068* (2013.01); *G06T 2207/20104* (2013.01); *G06T 2207/20212* (2013.01); *G06T 2207/30032* (2013.01)

(58) Field of Classification Search
CPC ......... A61B 5/062; A61B 10/04; A61B 10/06; A61B 2034/2065; A61B 2034/301; G06T 7/11; G06T 7/66; G06T 7/70; G06T 2207/10016; G06T 2207/10068; G06T 2207/20104; G06T 2207/20212; G06T 2207/30032

See application file for complete search history.

(56) References Cited

U.S. PATENT DOCUMENTS

| | | | |
|---|---|---|---|
| 2005/0259854 A1* | 11/2005 | Arimura | G06T 5/73 382/254 |
| 2009/0041320 A1* | 2/2009 | Tanaka | G06V 10/52 382/128 |
| 2013/0016092 A1* | 1/2013 | Collins | A61B 8/466 345/419 |
| 2013/0304446 A1* | 11/2013 | Rabinovitz | A61B 1/00158 703/11 |
| 2015/0119637 A1* | 4/2015 | Alvarez | A61B 34/30 600/102 |
| 2015/0138329 A1* | 5/2015 | Braun | A61B 1/0005 348/71 |
| 2018/0296281 A1* | 10/2018 | Yeung | A61B 34/32 |
| 2019/0228525 A1* | 7/2019 | Mintz | A61B 6/032 |
| 2021/0275000 A1* | 9/2021 | Ramesh | A61B 1/00059 |
| 2022/0031270 A1* | 2/2022 | Cohen | A61B 5/065 |
| 2023/0020596 A1* | 1/2023 | Sakaguchi | G06T 7/0012 |
| 2023/0410334 A1* | 12/2023 | Nishimura | G06T 7/50 |

OTHER PUBLICATIONS

Image based assessment of uncertainty in quantification of carotid lumen (Year: 2018).*

* cited by examiner

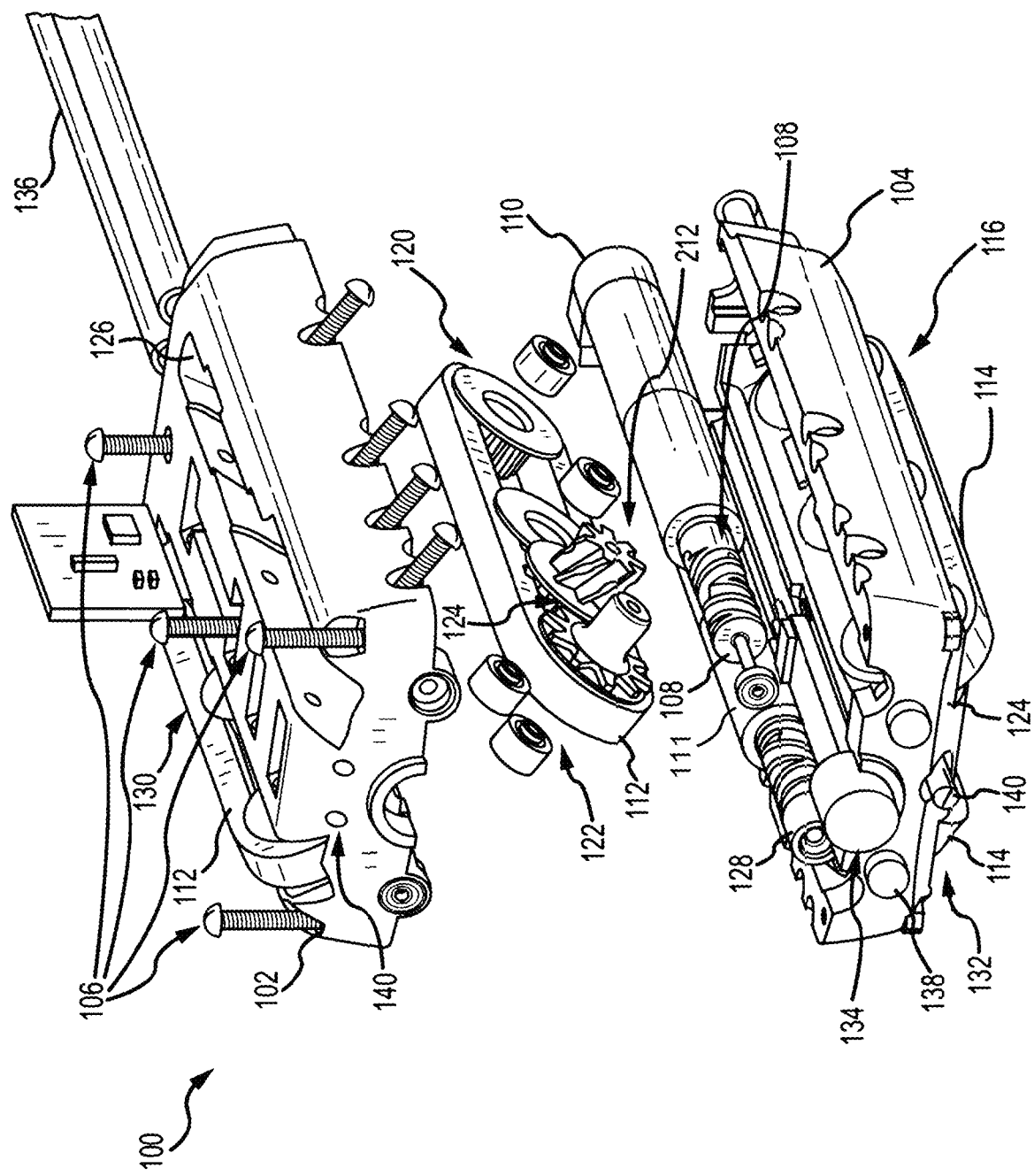

AUTONOMOUS NAVIGATION AND INTERVENTION IN THE GASTROINTESTINAL TRACT

CROSS REFERENCE TO RELATED APPLICATIONS

The present application claims priority to U.S. Provisional Patent Application No. 63/133,535, which was filed on Jan. 4, 2021, and is entitled Autonomous Navigation and Intervention in the Gastrointestinal Tract. The contents of the above-mentioned patent application are hereby incorporated by reference in its entirety.

GOVERNMENT SUPPORT

This invention was made with government support under grant number 1849357 awarded by the National Science Foundation. The government has certain rights in the invention.

FIELD

Embodiments of the present invention generally relate to self-propelled endoscopes and endoscopic devices for use in endoscopy procedures, and more specifically, to manipulating, controlling and more generally, easing the accessibility and use of self-propelled endoscopes and endoscopic devices.

BACKGROUND

Endoscopy procedures are the standard method of diagnosing and treating for a variety of lower gastrointestinal (GI) diseases, including colorectal cancers that remain the third most diagnosed and fatal cancers worldwide. Traditional endoscopes and colonoscopes are typically used to diagnose and treat a host of gastrointestinal (GI) diseases. While many attempts have been made towards developing less invasive alternatives to these devices such as wireless capsule endoscopes (WCE)'s, these systems are diagnostically limited due to their passive nature and do not offer the intervention capabilities of traditional scopes. Recent work towards robotic capsule endoscopes with the full diagnostic and treatment potential of conventional scopes has shown great promise, however the challenges of navigating these devices within the body remains. While substantial efforts have been devoted to achieving autonomous or assisted navigation of endoscopes to improve these procedures, these solutions have lacked the robustness and adaptability required of a medically adoptable autonomous or assisted navigation solution.

SUMMARY

An aspect of the present disclosure may include an autonomous endoscope system. The system may include a robotic endoscope device comprising a video camera, a microcontroller transmitting a control signal to control a movement of the robotic endoscope device, and a navigation computing device. The navigation computing device may, in response to receiving image data from the video camera, segment the image data, classify the segmented image data, estimate a center point within the segmented image data corresponding to an estimated center of a lumen within the image data, and instruct the microcontroller to control the robotic endoscope device based on the estimated center point within the segmented image data.

Another aspect of the present disclosure may include a method for autonomous colonoscopy intervention. The method may include the operations of modeling, using a magnetic sensor of a robotic endoscope device, a workspace of the robotic endoscope device and an end of a biopsy forceps and estimating, in relation to the modeled workspace, a location of a target polyp. The method may also include the operations of automatically adjusting, based on the estimated location of the target polyp, a pose of the robotic endoscope device and extracting, based on the modeled end location of the biopsy forceps and the estimated location of the target polyp, the biopsy forceps.

Yet another aspect of the present disclosure may include one or more tangible non-transitory computer-readable storage media storing computer-executable instructions for performing a computer process on a computing device. The computer process may include the operations of segmenting image data received from a video camera of a robotic endoscope device and classifying the segmented image data as at least one of a closed segment, a boundary closed segment, a boundary crossing segment, or an open segment. The computer process may also include the operations of estimating a center point within the segmented image data corresponding to an estimated center of a lumen within the image data and instructing, via microcontroller transmitting a control signal to control a movement of the robotic endoscope device, the robotic endoscope device to move based on the estimated center point within the segmented image data.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 1A illustrates an isometric, three-dimensional view of a robotic capsule endoscope according to one implementation.

It will be apparent to one skilled in the art after review of the entirety disclosed that the steps illustrated in the figures listed above may be performed in other than the recited order, and that one or more steps illustrated in these figures may be optional

DETAILED DESCRIPTION

In the following description of the various embodiments, reference is made to the accompanying drawings, which form a part hereof, and in which is shown by way of illustration, various embodiments of the disclosure that can be practiced. It is to be understood that other embodiments can be utilized.

Presented herein is visual navigation strategy and system for lumen center tracking comprising a high-level state machine for gross (i.e., left/right/center) region prediction and curvature estimation and multiple state-dependent controllers for center tracking, wall-avoidance and curve following. This structure allows a navigation system to navigate even under the presence of significant occlusion that occurs during turn navigation and to robustly recover from mistakes and disturbances that may occur while attempting to track the lumen center. The strategy is tested by a treaded and steerable robotic capsule endoscope (RCE) with the full toolkit of a conventional colonoscope, such as that described in U.S. patent Ser. No. 16/868,114, filed on May 6, 2020 and entitled "Robotic Capsule Endoscope", the entirety of which is incorporated by reference herein. One example of a treaded and steerable robotic capsule endoscope (RCE) is illustrated in FIGS. 1A and 1B.

Figure 1B:
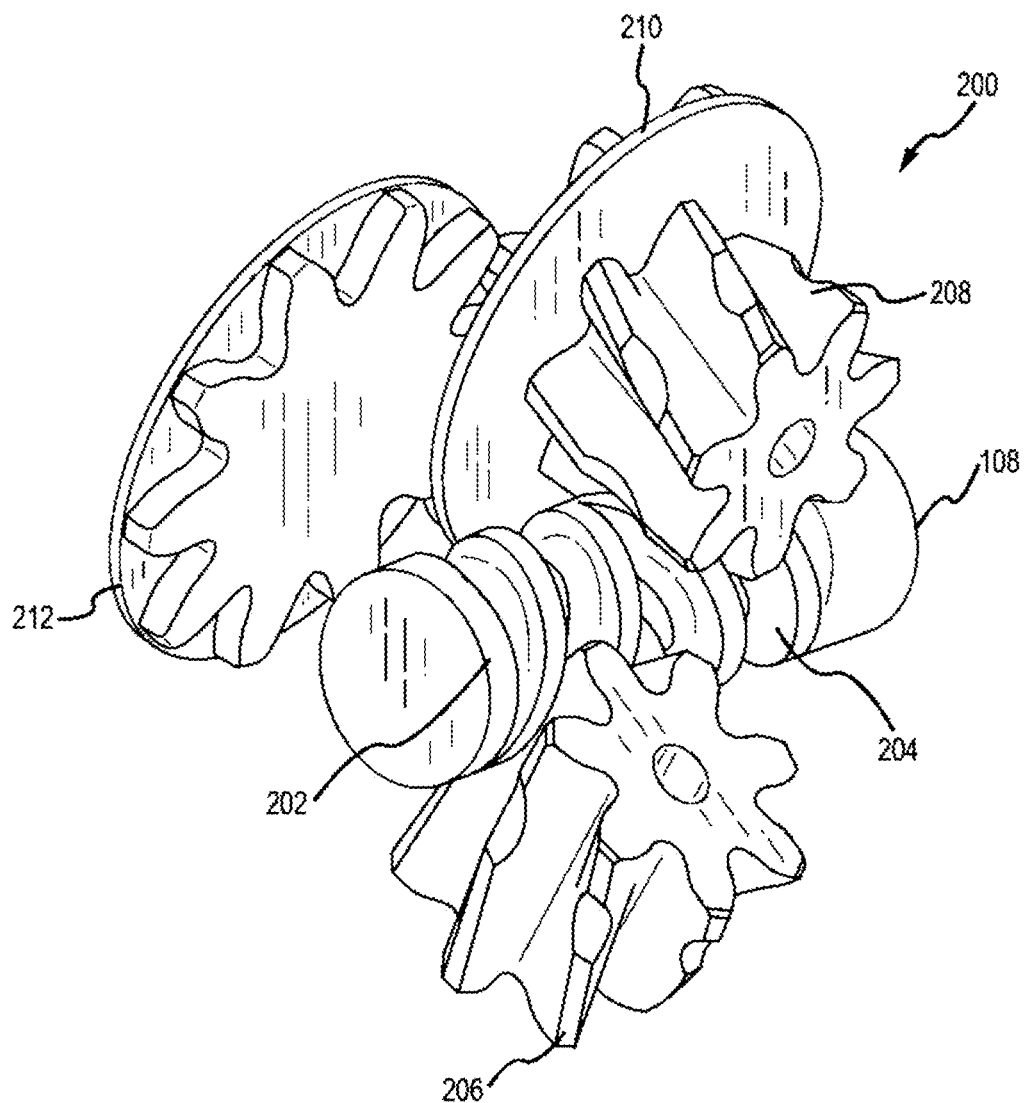
FIG. 1B illustrates an isometric view of a double worm drive mechanism with spur gear idling.

In particular, FIG. 1A illustrates an isometric, three-dimensional view of a robotic capsule endoscope 100 according to one implementation. As shown, the robotic capsule 100 may include a housing comprising an upper portion 102 and a lower portion 104. The upper portion 102 and the lower portion 104 may be fastened together in multiple locations by the machine screws 106, which provided clamping force to hold the upper portion 102 and the lower portion 104 together and the components within the housing. A first motor support shaft 108 may be disposed within the housing between the upper portion 102 and the lower portion 104. A motor 110 may be located on an end of the first motor support shaft 108 to rotate the shaft based on one or more control signals received at the motor. In some instances, the first motor support shaft 108 may include a first screw section comprising right-handed spiraling and a second screw section comprising left-handed spiraling. For example, FIG. 1B illustrates an isometric view of a double worm drive mechanism 200 with spur gear idling. As shown in the illustration, the first motor support shaft 108 includes a first portion including right-hand spiraling 202 and a second portion including left-hand spiraling 204. Rotation of the first motor support shaft 108 causes a corresponding right-handed spiraling of the first portion 202 and a left-handed spiraling of the second portion 204.

A first worm gear 206 may be engaged with the right-handed spiraling 202 of the first motor support shaft 108. As illustrated, a counter-clockwise rotation of the first motor support shaft 108 caused by the motor 110 may cause a corresponding counter-clockwise rotation of the first worm gear 206. Similarly, a second worm gear 208 may be threadably engaged with the left-handed spiraling 204 of the first motor support shaft 108. The same counter-clockwise rotation of the first motor support shaft 108 discussed above may cause a corresponding counter-clockwise rotation of the second worm gear 208.

Returning to FIG. 1A, the overall shape of the capsule-shaped robot 100 may be cylindrical (i.e., longer than it is wide). To achieve this shape, the motor 110 may be oriented parallel to the treads 112, 114 that are powered by the motor. Further, to reduce gear forces and generate the smallest possible space claim, the first motor support shaft 108 is used. A single motor drive shaft can transmit power to multiple worm gears 206, 208, and thus a single motor 110 can drive the top tread 112 and bottom treads 114 in the same rolling direction. To further conserve space and reduce complexity, the "double-worm" drive discussed above is used that includes both right-hand 202 and left-hand spiraling 204.

A continuous track assembly 116 may be threadably engaged with the first motor support shaft 108 to rotate a tread or track 114 to propel the capsule robot 100. The continuous track assembly 116 may include the first worm gear 206, one or more pulley gears 120, and a continuous track 114 driven by the rotation of the first worm gear 206 about the one or more pulley gears 120. For example, motor 110 may, in some instances, rotate the first worm support shaft 108 in a counter-clockwise direction about the shaft axis. Through the right-handed spiraling 202, first worm gear 206 similarly rotates in a counter-clockwise direction. Tread 114 may similarly rotate in a counter-clockwise direction in response to the rotation of the first worm gear 206. As shown in FIG. 1A, the treads 114 may extend from the lower portion 104 of the housing through a first angled continuous track slot 124 included in the lower portion of the housing. The angled continuous track slot allows for a portion of the lower continuous track assembly 116 to extend from the lower portion 104 of the housing to engage with a surface, such as an inside surface of a GI tract. The rotation of the treads 114 of the continuous track assembly 116 in this direction may thus propel the robotic capsule in a first direction through the activation of the motor 110 and rotation of the first worm support shaft 108.

Figure 2:
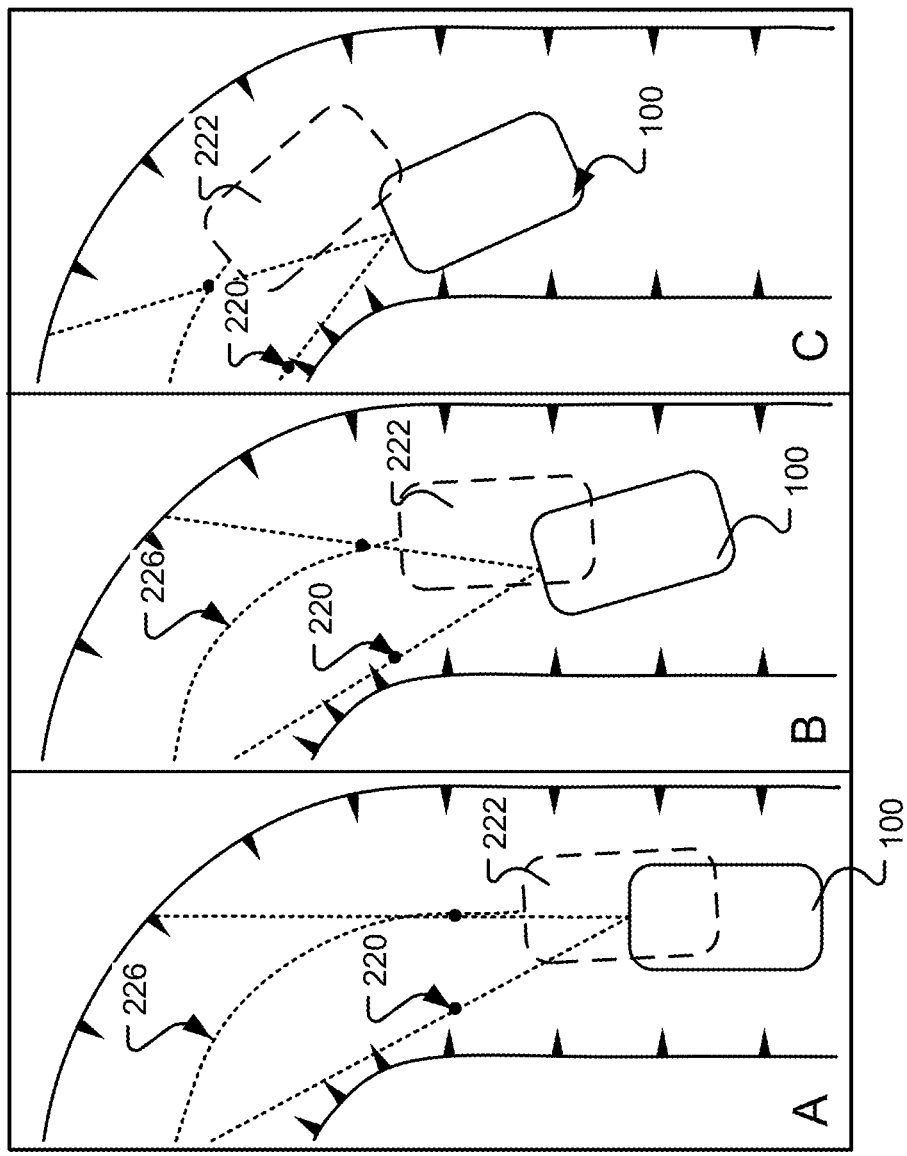
FIG. 2 illustrates a robotic capsule endoscope in a lumen navigating an upcoming turn.

Although the double worm drive concept with opposite handed gear interactions produces favorable forces, the top treads 112 and bottom treads 114 will no longer rotate in the same rolling direction (as best seen in FIG. 2). That is, if the bottom treads 114 are rolling the device 100 forward, the top treads 112 would be attempting to roll it backward, thus causing the device to retroflex instead of propelling it in a single direction. Thus, the capsule robot 100 may include one or more idler gears 210, 212 into an upper continuous track assembly 122, thereby regaining similar rolling directions for both the lower treads 114 and the upper treads 112.

In some embodiments, the treads 112, 114 of the continuous track assemblies 116, 122 may include micropillared polydimethylsiloxane (PDMS) timing-belt style treads. The micropillared PDMS treads may be used in response to the slippery, mucosa surface upon which the capsule robotic device 100 is deployed. Further, a slight angle is provided for the continuous track assemblies 116, 122 to improve traction on the surface of the environment in which the device 100 is deployed. For example, rather than a flat planar surface that conventional vehicles encounter, the colon mucosa, although variable, is often elliptical or semi-rounded in nature. Providing the continuous track assemblies 116, 122 on a slight angle may improve the traction on such irregular, deformable surfaces.

In some embodiments, a second motor 111 and a second worm support shaft 128 may be included to drive a second upper continuous track assembly 130 and a second lower continuous track assembly 132. The operation and design of the second upper continuous track assembly 130 and a second lower continuous track assembly 132 may mirror that described above. The second upper continuous track 130 may extend through an angled slot of the upper portion 102 of the housing. In some embodiments, the second angled slot of the upper portion 102 of the housing may be substantially perpendicular to the first angled slot and the second angled slot of the lower portion 104 of the housing may be substantially perpendicular to the first angled slot.

The second motor and second worm support shaft 128 provides for 2-DOF locomotion through skid-steering with independently controlled left and right treads. This has the added benefits of improving the balance of the capsule robot 100 (i.e., the heaviest components of the assembly, the motors, can be placed far from the center of gravity) and allowing for an increased turning moment. Each of these motors may power treads above and below the capsule robot 100 allowing for omni-directionality may be useful in a collapsed lumen, which is the natural uninflated state of the intestine.

One or more additional features or devices may be included in or on the capsule robotic device 100 for use in colonoscopy procedures. For example, a camera device 134 may extend from a front portion of the housing for collecting video or photographs during a procedure in which the capsule robot device 100 is used. Information obtained by the camera, such as a live video feed, may be transmitted to a display device for analysis by a technician. One or more lighting devices 138, such as a light-emitting diode (LED), may be included in the device 100 to provide lighting for video and/or photography by the camera 134.

In one example, the robotic device 100 may be untethered and include wireless capabilities to provide the video feed. In another example, a wire may be included in a flexible tether that extend from the rear of the device 100. The flexible tether may house any number and type of wires, tubes, or other transporting media for use by the robotic device 100. The wires housed in the tether may be connected to a video processing device and/or display for use by a technician during a colonoscopy procedure. In another example, the tether may house one or more motor control wires for transmitting control or activation signals to the motors 110 of the capsule device 100. Through transmission of control signals to the motor 110 along the tether, the movement of the capsule robotic device 100 may be controlled.

The tether may also include an air tube, a water tube, or a combination of air and water tubing 136. The air/water tubing 136 may transport air (for inflation of an intestine) and/or water (for cleansing of an area) during a procedure. One or more air/water channels/spouts 140 may be located on the front of the device 100 to provide for delivery of the air/water carried on the air/water tubing 136. A tool port 140 may also be disposed on the front portion of the device 100 for activation of one or more tools associated with a colonoscopy procedure. For example, a forceps tool may be integrated with the tool port 140 for collecting biopsies during a procedure. The forceps may be controlled through the tool port 140, which may include a control line housed within the tether trailing the robotic device 100. Control signals transmitted on the control line may activate one or more tools integrated with the tool port 140. Other tools may also be used with the device 100, including snares, tattoo needles, and the like).

A wide range of attempts have been made to develop autonomous visual navigation solutions for flexible and capsule endoscopes 100 (such as that described above with relation to FIGS. 1A and 1B), including lumen centralization methods and feature tracking methods. Unfortunately, many of these strategies have failed to perform in real-time due to computational constraints, or struggle to perform when the lumen center is not immediately visible. The most common methods for autonomous endoscope navigation have focused on darkest or deepest region techniques in which the darkest and/or deepest region in an image is identified and used as the goal for adjusting endoscope heading. While success has varied widely, these approaches suffer from a fundamental flaw in making the assumption that the region of greatest depth within any given image represents a useful goal for immediate heading adjustment. While reaching the deepest point in an image may be a very reasonable goal for endoscope navigation on a larger scale, the lighting conditions, focal length of the endoscopic camera, and geometry of surrounding tissue all have a significant impact on how far away this maximum depth goal may be. As depicted in FIG. 2, an RCE 100 may be controlled by a control algorithm that is solely based on perfect alignment of the camera towards the deepest point in every image, illustrated by line 220 through traversals A-C. However, such an algorithm may ignore both the size of the endoscope 100 itself and the 3D structure of the surrounding anatomy, and thus will inherently limit the ability of the scope to progress down the lumen. A heading control algorithm may instead attempt to align the front end of the scope parallel to the lumen walls at all times so as to allow for both mobility and visualization (as shown by the transparent RCE 222 in FIG. 2 along heading line 226). However, maximum depth estimates may only achieve this goal when there is no perceivable curvature in the upcoming tissue (i.e., long, straight sections). Lumen centralization methods using the edges or contours of structures surrounding the lumen have also been demonstrated. These methods provide a more useful goal for immediate heading adjustment in that the surrounding structures are by definition much closer to the camera than the point of maximum depth, however large structures like haustral folds may not always be present in images particularly under the presence of occlusion and during sharp turns when an endoscope faces the colon wall for much of the maneuver.

A robust navigation algorithm may be able to handle a difficult and diverse set of structural environments within an anatomy that can vary widely between patients. While well-centered views of the colon may show significant structure, the tight turns and deformability of the colon may result in a large percentage of images not being well-centered in the lumen, but may instead show close views of the lumen wall, resulting in an occluded camera with no view of the larger structure. To account for these difficult cases, aspects of the present disclosure involve, systems, devices, methods, and the like for a state dependent region estimation method based on an explicit analysis of the large structures present in each image. This system comprises a high-level state machine for gross region prediction, a turn estimator for anticipating sharp turns, and several lower level controllers for heading adjustment. From this structure, the system is able to utilize lumen centralization control approaches when the device has clear views of the lumen, while employing alternative estimation/control approaches around sharp curves. The system and method provide for navigation of a RCE device 100 to operate even under the presence of significant occlusion from the lumen wall (when accurate lumen center estimates are much more difficult to make) and to anticipate and respond to upcoming turns, typically without user intervention.

Figure 3:
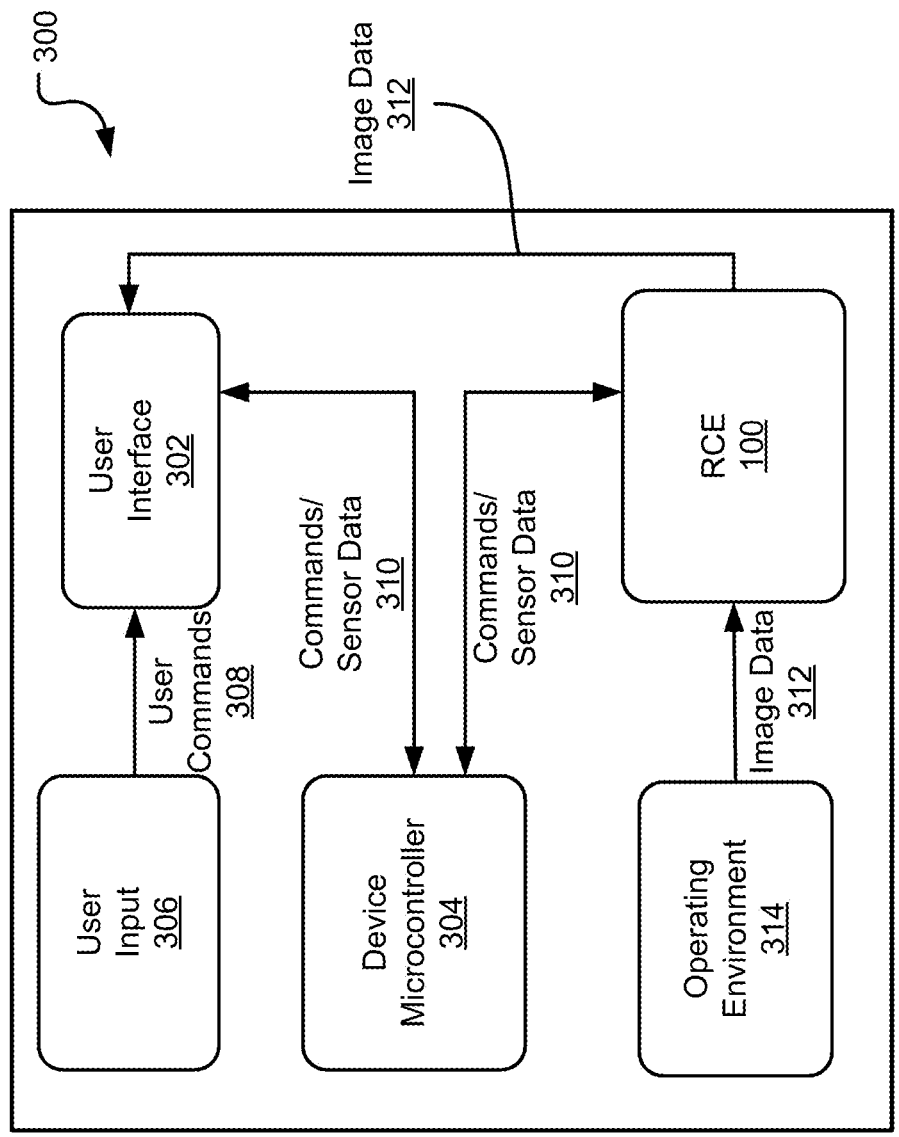
FIG. 3 illustrates an overview of the robotic capsule endoscope system, including the joystick input controller, a laptop, external hardware and the robotic capsule endoscope.

Aspects of the present disclosure are utilized in conjunction with an RCE device 100 and control system of the RCE device. In one particular implementation, the RCE design 100 may include DC micromotors to allow for left/right steering of the device. In one implementation, a small camera 134 and one or more LEDs 138 may be housed in the front of the device, and an inertial measurement unit may be housed in the top of the chassis. One or more onboard motor encoders allow for measuring individual motor speed. The RCE 100 also incorporates tool ports 140 for biopsy forceps/snares, suction, irrigation and insufflation. The RCE 100, a simulator, and additional system components are shown in FIG. 3. The RCE 100 may similar to that described above with relation to FIGS. 1A and 1B. The RCE 100 may include a dual motor driver, current sensors for estimating motor torque, an offboard solenoid for controlling insufflation, and two switching transistors for controlling LED brightness and the offboard solenoid. In one implementation, the RCE 100 may be controlled externally via a user interface 302 via a Wi-Fi enabled device in communication with an onboard or separate microcontroller 304. During control of the RCE 100, one or more user commands 308 may be received as user input 306 and provided to the user interface 302. The user interface 302 may communicate with the microcontroller 304 to provide one or more of the received commands or one or more generated control commands. The microcontroller 304 may process and/or transmit the commands 310 to the device 100 to control the device operations. Further, image data 312 may be obtained from the operating environment 314 by the RCE 100, such as through a camera or any other sensor of the RCE. The image data 312 may then be transmitted to the user interface 302 for display on a display device. Sensor data 310 may also be obtained by the RCE 100 from the operating environment 314 and provide to the device microcontroller 304 that may process the sensor data 310 or provide the sensor data to the user interface 302 for display. These and other operations of the RCE 100 are described in greater detail herein.

Although the methods and systems are described herein with reference to a robotic capsule endoscope device 100, it should be appreciated that the techniques and systems may also utilize a more conventional flexible endoscope device, such as one utilizing a tether to connect the endoscope to a computing device. In general, the techniques, methods, systems, and the like described herein may be applicable to any type of known or hereafter developed endoscope device with autonomous capabilities.

Figure 4:
FIG. 4 illustrates a user interface displaying video images obtained from a robotic capsule endoscope system.

A custom interface 302 for sending and receiving user commands 306 and/or autonomous control commands to/from the RCE 100 and for collecting and visualizing raw/processed video as well as other data from the RCE system may be provided. One implementation of the user interface 302 is illustrated in FIG. 4. In particular, the user interface 302 may be displayed on a display device 402 of a computer 404, such as a laptop or desktop computer. A user can interact with the interface 302 via an input device in communication with the computer 404. Once the system is running, the RCE 100 may be solely controlled from the input device and the user may be able to begin/stop a test run, steer each side of the device motors independently (tank steering), adjust max motor speed, adjust LED brightness, insufflate, and record snapshots and video, among other options, through user inputs 306. In addition, for testing control strategies, the user is able to enter/exit autonomous control modes of the RCE 100. Feedback to the user may be provided via the user interface 302, which overlays user selectable information including but not limited to: estimated viewing region/lumen center estimated position, the number of segmented haustral folds, predicted motion, and/or current operating mode/settings of the device 100 (auto, manual, LED brightness, max motor speed, etc.).

Figure 5:
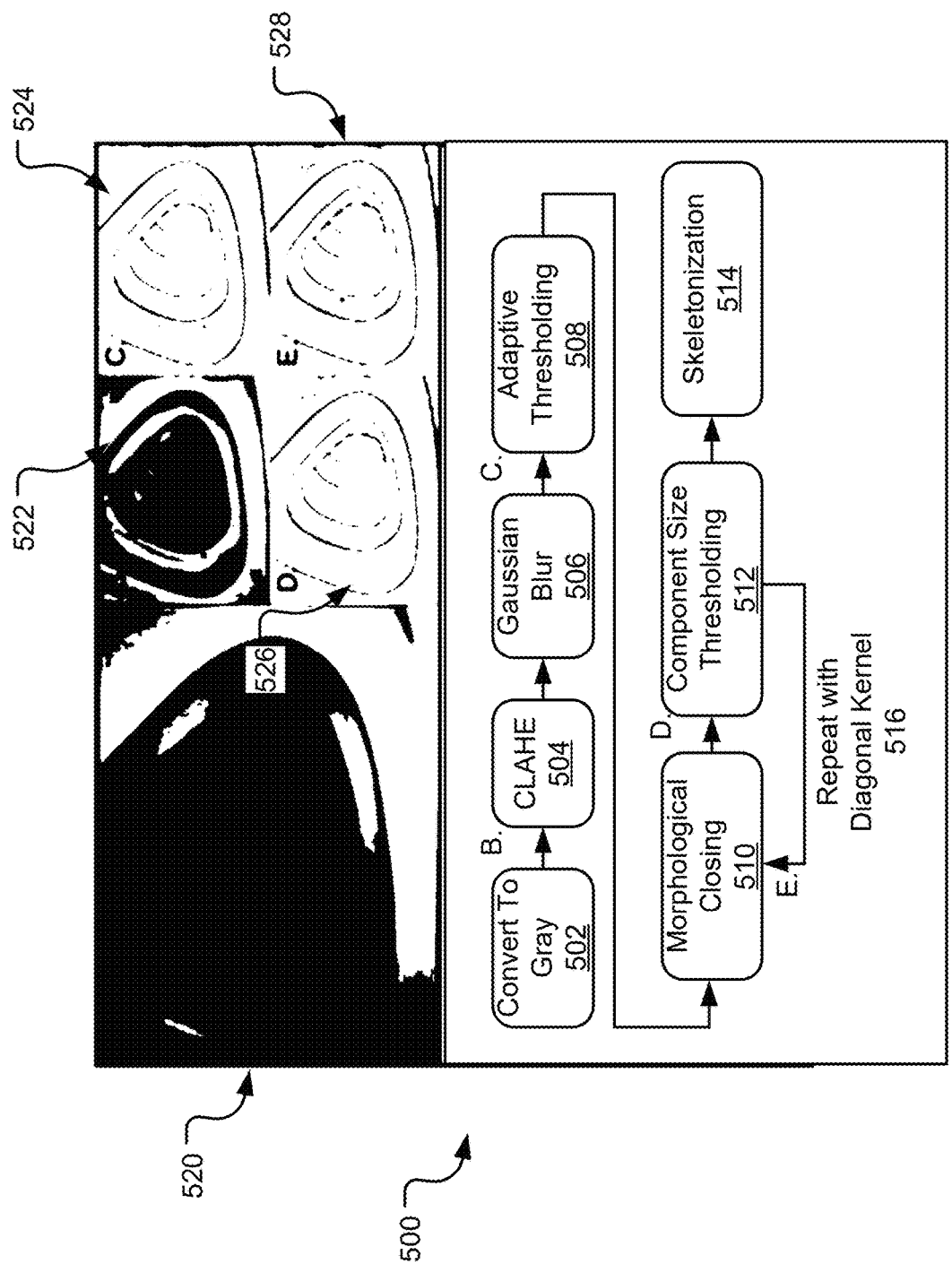
FIG. 5 is a flowchart of operations for preprocessing of images and resulting images from the preprocessing operations.

The RCE system 300 described above may be used to process images from the camera of the RCE for controlling or navigating the RCE. Initially, image data 312 from the video may be pre-processed and segmented. In one example, each image of the image data 312 may be preprocessed through the steps illustrated in FIG. 5. In one particular implementation of the method, each received color image 520 may first be converted to grayscale at operation 502. A Contrast Limited Adaptive Histogram Equalization (CLAHE) technique may then be applied over the image at operation 504, which breaks the image into 144 tiles (12×12) (as shown in panel B 522 of FIG. 5). A Gaussian blurring filter may then be applied at operation 506 to this contrast adjusted image to complete the preprocessing steps. To segment the image, a mean adaptive thresholding method may be utilized at operation 508 to determine the appropriate threshold at each pixel using a local neighborhood of size 9×9 px (as shown in panel C 524 of FIG. 5). A morphological closing of the image is performed at operation 510 using a small square kernel, and then connected components of less than 200 px may be removed to reduce the noise in the image at operation 512. These operations may be repeated using a diagonal kernel to attempt to connect some of the remaining large components and remove any residual noise from the image (as shown in panels D-E 526-538 of FIG. 5). This segmented image may than be skeletonized at operation 514 to reduce each segment to 1 px in width. Finally, a simple filter is used to identify junctions and endpoints in each skeletonized segment. The image segments may then be pruned to remove branches as large as 8 pixels. An additional result of this pruning is that segments without endpoints are identified and flagged as closed curves.

Figure 6:
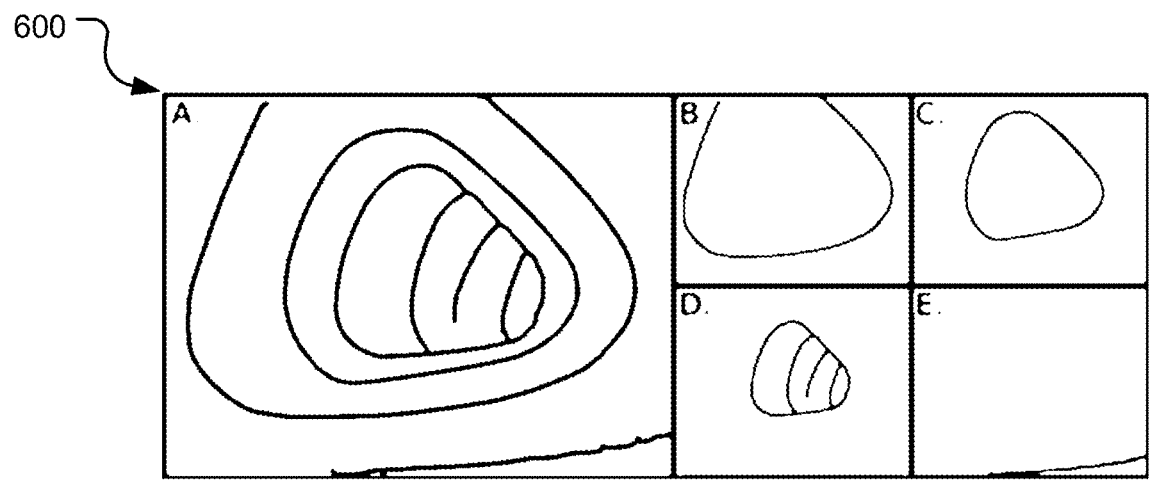
FIG. 6 illustrates image segments for a single segmented image resulting from preprocessing of the image.
Figure 7:
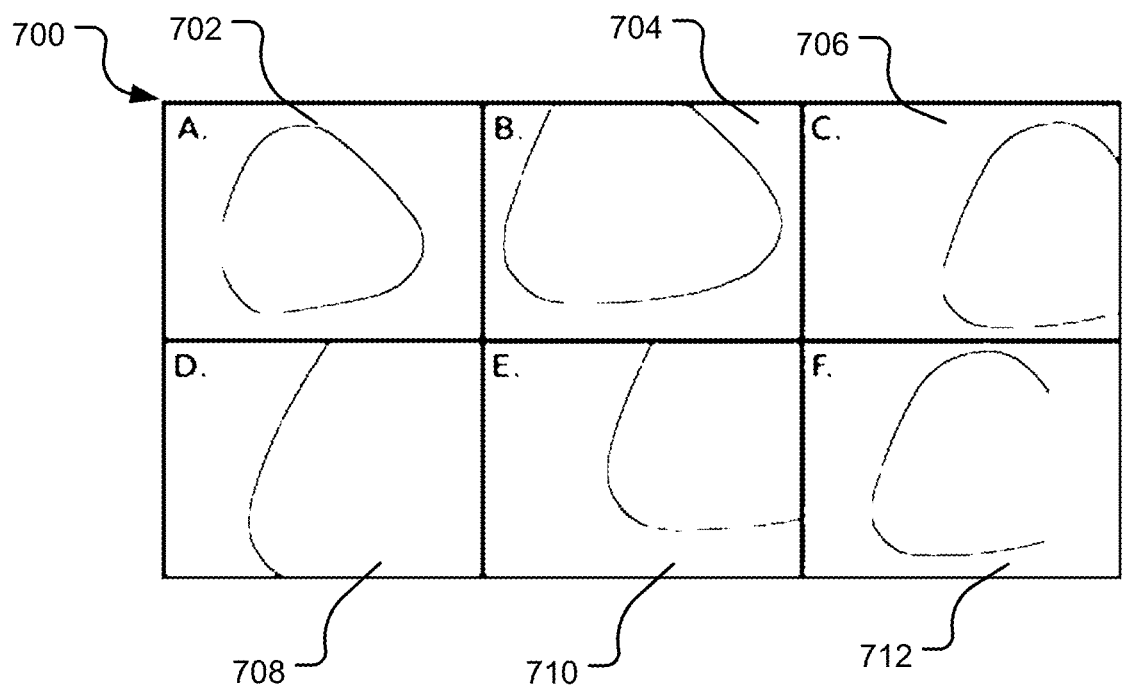
FIG. 7 illustrates different image segment types resulting from preprocessing of the image.

Once segmentation is complete, each image segment may be considered independently before being combined with all other segments to finalize lumen center estimates. An example segmented image 600 is shown in FIG. 6 and example segment classes 700 are shown in FIG. 7. Segments may be classified into one of several types of segments and based on that classification, different properties of each segment may be used to estimate the lumen center. This classification process is particularly useful, not only for the different ways these segment types can be used, but also due to the accuracy different types provide. As there is no guarantee that a frame will contain the more accurate segment types (closed, o-closed, b-closed), it may still be useful to consider estimates from each of the less accurate segments (b-crossing, open). Thus, the goal of classification is to obtain a final estimate of the lumen center that is based on the most useful segments in any given frame, while also ensuring that each segment type is used to the best of its ability. The following describes one example process of classifying these segments and is followed by a description of how each segment type is utilized.

Closed Segments: Segments that form a complete closed curve are designated as closed segments (as shown in panel A 702 of FIG. 7). To determine when segments are closed, an image convolution may be done on the skeletonized image 528. This convolution flags pixels when they occur at a segment end, and thus any segments with no ends are considered to be closed while those that do have ends are considered to be some other segment type. While pruning of the skeletonized image 528 during the preprocessing steps, this operation allows the system to avoid incorrectly classifying closed segments which may initially have some residual branches and thus some end points. Generally, if a closed segment is missed due to a branch, it will typically be caught during the open segment process and re-categorized as described below Boundary Closed Segments: In general, many segments tend to partially intersect the boundary of the image frame. A segment that intersects the same boundary (e.g., the right side of the frame) at two distinct points may be classified as a boundary closed or b-closed segment (as shown in panels B-C 704-706 of FIG. 7). The distinct intersection points of these segments with the frame may be a minimal distance apart to ensure that they are not simply branching or running along the boundary. In one example, a threshold distance of 100 pixels separation between intersections points may be set for segments to be categorized as a closed segment.

Boundary Crossing Segments: When the camera 134 of the RCE 100 is close to a haustral fold, it may be possible that the segmented fold crosses multiple boundaries of the image frame. These may be considered to be boundary crossing or b-crossing segments when they run the full width or height of the image (i.e., crossing both the top and bottom or right and left boundaries), and corner crossing or c-crossing segments when they cross two adjacent boundaries such as the top and right boundary of the image. A boundary crossing segment is illustrated in panel D 708 of FIG. 7 and a corner crossing segment is illustrated in panel E 710. This designation may be applied after ensuring that segments do not otherwise belong to another categorize as a closed or a b-closed segment. In some instances, a more liberal requirement may be placed on these segments such that they may be categorized as b-crossing or c-crossing if they are within 10 pixels of two distinct image boundaries.

Open Segments: If a segment does not intersect multiple image boundaries and cannot be designated as closed or b-closed, the segment may be considered to be an open segment and some additional processing may be performed to determine how the image is used (as shown in panel F 712 of FIG. 7). While many open segments may be very useful, segments left over from folds that are not well-segmented and thus mostly filtered out may be less useful and may offer poor or misleading center estimates if they are used incorrectly. Therefore, more useful/trustworthy open segments may be separated from noisy/misleading segments. More trustworthy open segments may come in several forms. If, for instance, a segment is nearly closed but has been left open (perhaps due to a poor segmentation or because the segment is physically open at a point) it may still provide good estimates. Additionally, if a segment forms a closed shape but includes residual branches (due to incomplete pruning or inner branching segments), it may also provide good estimates. Several characteristics may be considered when deciding if an open segment should be considered trustworthy and thus effectively "closed," including but not limited to the aspect ratio, size and extrema points.

Aspect ratio may also be considered to determine if a segment is a small residual piece of a bad segmentation. In particular, considering the size (height and width) of the image aids in ensuring that the segment is not the result of over segmentation resulting in some odd shaped multibranching segment. In addition, the eight extreme points of the segment (top-left, top-right, right-top, right bottom etc.) may be considered to ensure that a segment is complete enough to allow a useful shape fit. These extreme points (as determined by the segments intersection points with a bounding box) are generally unique for a smooth, nearly closed curve typically generated by the complete segmentation of a well centered haustral fold. For open segments, however, these extrema will not be unique when, for example, the segment terminates at the edge of its bounding box (e.g., a segment without a top and right side may only have 4 unique extreme points, left-top, left-bottom, bottom-left, bottom-right). Thus, the number of unique extrema present in the segment can rapidly provide a sense for how many sides of a segment exist and how closed the segment may be. Those segments which meet the aspect ratio, size, and extrema considerations may be considered as good candidates for artificially closing via shape fitting (either with an ellipse or a triangle) and may therefore be designated as o-closed segments. If an open segment does not meet these considerations or if the shape fit results in a poor fit (as described below), it may be classified as open.

This process of attempting to close open segments may occur for several reasons. While simulator images may show many closed curves, in vivo, these shapes may be less common and provide the ability to predict the lumen center without relying fully on closed segments. In addition, the segmentation approach described earlier is intended to be conservative with the goal of identifying and selecting the strongest edges in each image while filtering out any smaller/less prevalent segments. This can lead to unintentionally under-segmenting structures that would otherwise appear as closed in an image and results in opening segments that should be closed. The process of closing open segments provides a correction for these issues without increasing the complexity and computation time of the segmentation.

Once the segments have been classified, the specific properties of each segment type may be used to form an estimate on the camera 134 orientation with respect to the lumen. Thus, each segment's characteristics may be used to estimate the camera's center offset $X_{est}$ and $Y_{est}$ from the lumen center (although some segments may not be able to provide useful estimates on both degrees of freedom). While there may be some translational components to these offsets (due to the relative size of the RCE 100 in the lumen), the ability to translate is considered marginal and thus the offsets may be evaluated as purely angular rotation scaled based on image width W and height H and the camera's total field of view, as obtained through equation (1):

$$\alpha = \frac{FOV}{W}, \beta = \frac{FOV}{H} \quad (1)$$

Figure 8:
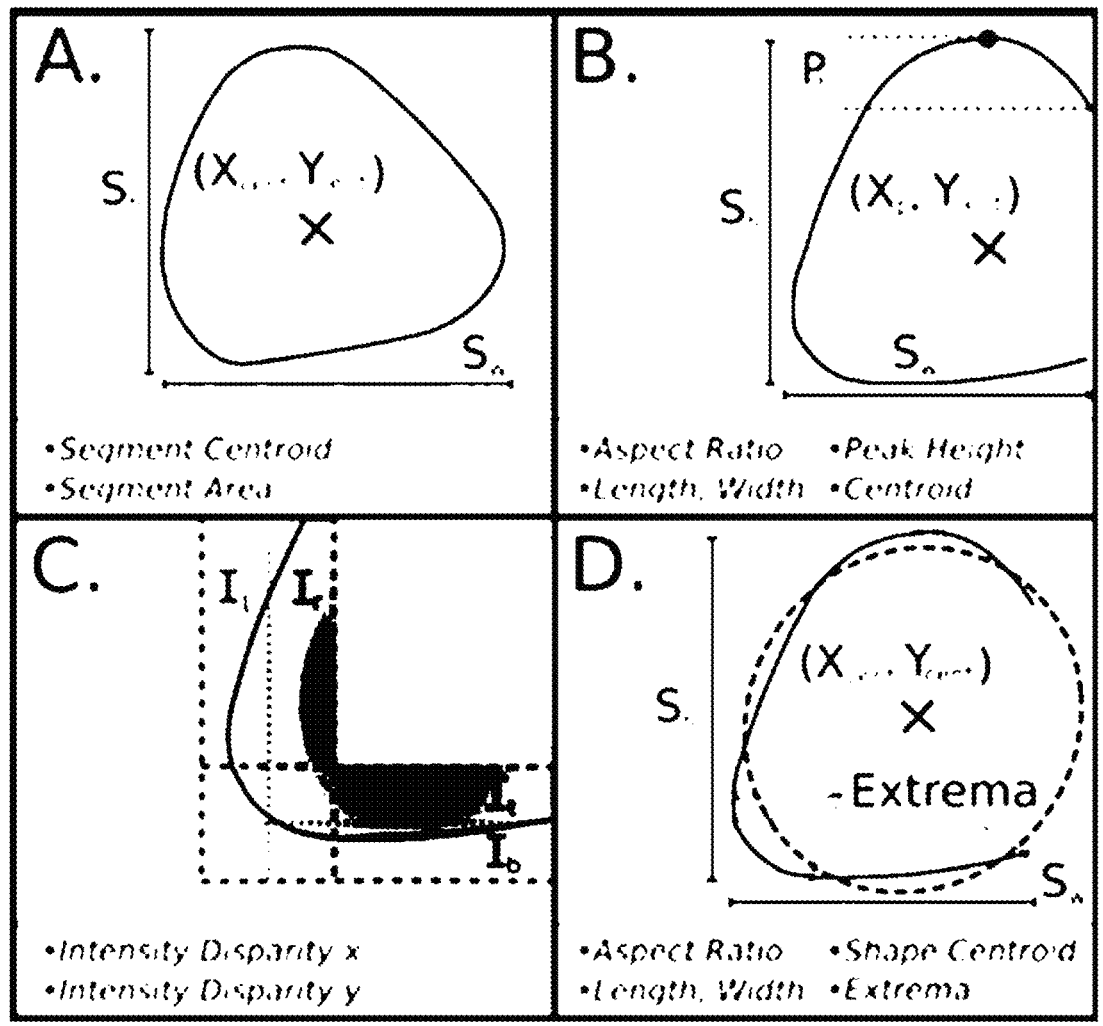
FIG. 8 illustrates different image segment class/type and the respective properties of the corresponding segment type.

These individual estimates may later be weighted and combined based on the relative accuracy of each segment type. FIG. 8 provides a summary 800 of the various properties selected for each segment class.

Figure 9:
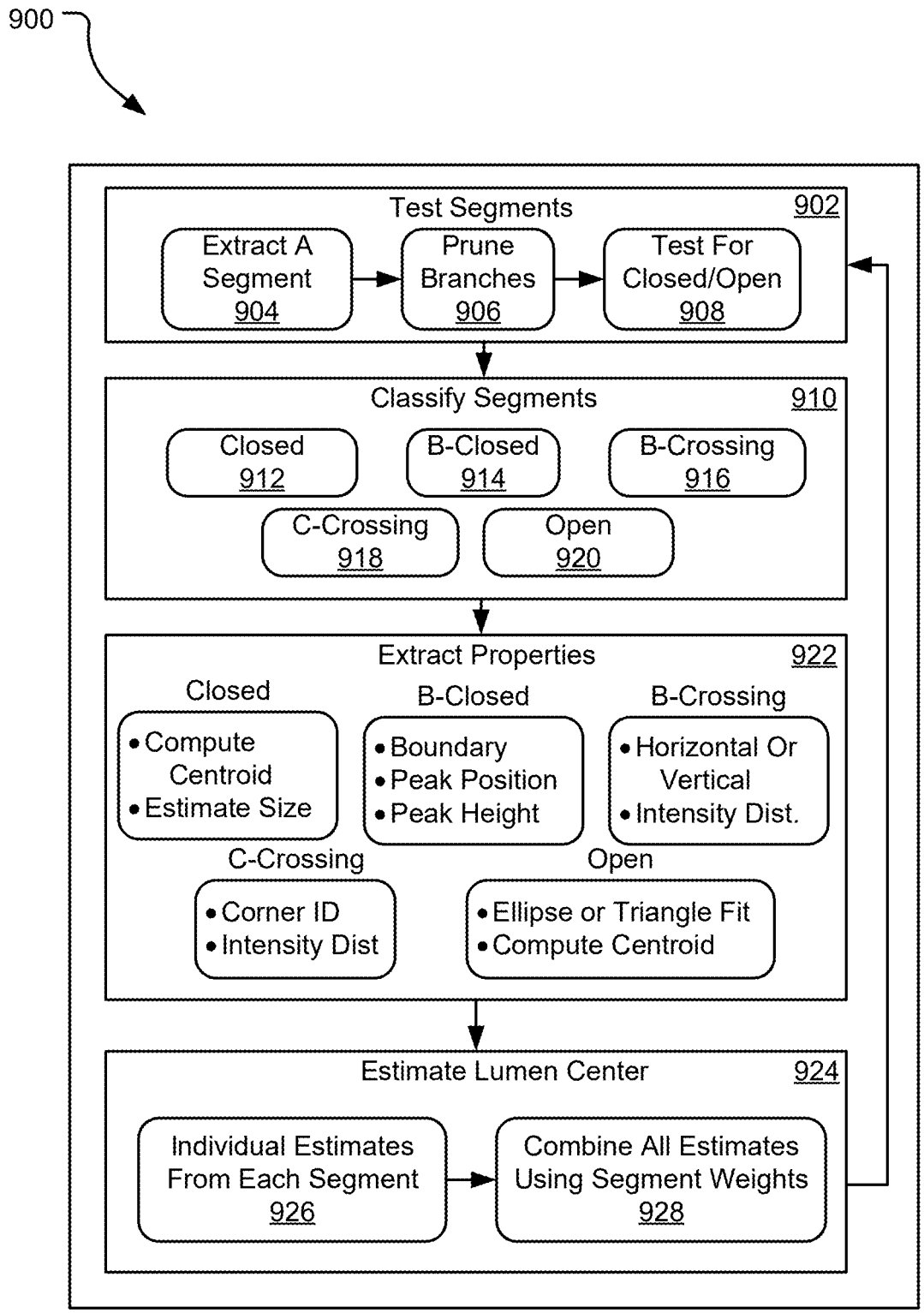
FIG. 9 is a block diagram of a region estimation algorithm following the pre-processing of the color image.

FIG. 9 illustrates one method 900 for the segmentation, classification, and center estimation strategy. In particular, section 902 illustrates the operations for testing the segments, including the operations of extracting a segment 904 from the image, pruning branches 906, and testing the extracted segment for closed/open features 908, as described above. For each segment, a classification of the segments in section 910. In particular, the segments may be classified as closed segments 912, b-closed segments 914, b-crossing segments 916, c-crossing segments 918, or open segments 920, as also discussed above. Once classified, one or more properties of the segments may be extracted, as illustrated in section 922 and discussed in more detail below. The extracted properties may be used to estimate the camera's center offset form the lumen center at section 924 by generating individual estimates from each segment 926 and combining the estimates using segment weights 928. The process of estimating the lumen center 924 is also described in more detail below. The process 900 of FIG. 9 may return to section 902 to be repeated for additionally received images.

Due to the conservative nature of the segmentation process, closed segments 912 are indicative of very well-defined haustral folds. These segments 912 can thus provide useful information about the lumen center location by simply computing the centroid of the segment over all n segment points $(x_i, y_i)$. As shown in equations:

$$X_{cl} = \alpha \left( \frac{W}{2} - \frac{1}{n} \sum_{i=1}^{n} x_i \right) \quad (2)$$

$$Y_{cl} = \beta \left( \frac{H}{2} - \frac{1}{n} \sum_{i=1}^{n} y_i \right) \quad (3)$$

a comparison of the centroid of the segment to the center pixel of the image $$\left( \frac{W}{2}, \frac{H}{2} \right)$$

may be made, and the magnitude and sign of this error estimates how far and in what direction the camera is off-center from the lumen.

The quality and type of camera 134 orientation estimates provided by boundary intersecting segments 914, 916 may be dependent on the specific class of these segments such the class of each segment may be considered separately. B-closed segments 914 are similar to truly closed segments and thus also provide accurate information. Preliminary testing within a simulator shows that when the size $S_{sz}$ of a b-closed segment 914 effectively spanned 80% or more of the frame area $I_{sz}$ (such as that shown in panel B 704 of FIG. 7), the system 300 may reliably fit a shape to this segment, compute the centroid of that shape, and complete the analyses using equations (4a), (5a) included below. This, however, represents a minority of these segment types 914, which typically do not fill most of a frame. A more typical b-closed segment 914 is shown in panel C 706 of FIG. 7. This right b-closed segment 914 (one that intersects the right boundary of the image) is generally indicative of a camera that is facing left of the lumen center, but without some other information it may be difficult to determine how far left of center the camera is pointed. To improve this estimate, a peak height $P_h$ of the segment 914 may be considered. For determining $X_{bcl}$ for segments bounded by the right or left image boundary, large peaks may be considered to occur when enough of the top of the haustra is visible that the resulting segment begins its downwards slope before hitting the image boundary. By considering the top-most extreme points and the right boundary intersection point and computing the pixel difference, the system 300 can determine if the segment 914 reaches a peak and how large that peak is. If this peak height $P_h$ is above a fixed threshold, the system 300 may consider it large enough to make a center prediction in the x-direction and estimate the lumen center to be the x-position of the peak, $x_{pk}$ (considered to be the mean of the top most extrema), using equation (4b) below. For these segments closed by a vertical boundary such as panel C 706 of FIG. 7, the y-centroid position may be used to estimate the error in the y direction. For b-closed segments 914 intersecting a horizontal, rather than a vertical boundary, the method 900 may be flipped to estimate the x-error from the x-centroid of the segment, and the y-error via the peak identification approach described above, using equation (5b) below. In this manner, the method may be applied to b-closed segments 914 on the top, bottom, left or right of the image.

$$X_{bcl} = \begin{cases} \alpha \left( \frac{W}{2} - \frac{1}{n} \sum_{i=1}^{n} x_i \right), & \text{for } \frac{S_{SZ}}{I_{SZ}} > 0.8 \quad (4a) \\ \alpha \left( \frac{W}{2} - x_{pk} \right), & \text{for } P_h > 20 \quad (4b) \\ 27.5 + \alpha \cdot S_h \left( 0.5 - \frac{S_w}{S_h} \right) & \text{for } P_h < 204 \quad (4c) \end{cases}$$

$$Y_{bcl} = \begin{cases} \beta \left( \frac{H}{2} - \frac{1}{n} \sum_{i=1}^{n} y_i \right), & \text{for } \frac{S_{SZ}}{I_{SZ}} > 0.8 \quad (5a) \\ \beta \left( \frac{H}{2} - y_{pk} \right), & \text{for } P_h > 20 \quad (5b) \\ 27.5 + \beta \cdot S_w \left( 0.5 - \frac{S_h}{S_w} \right), & \text{for } P_h < 204 \quad (5c) \end{cases}$$

If a large peak is not present in a b-closed segment 914, the system 300 may not use the previously described method to estimate the lumen center. Rather, the system 300 may make the assumption that the center occurs near or past the intersection of the frame and the b-closed segment 914. This indicates that the camera 134 orientation is offset from the lumen center by at least half of the camera's field of view (FOV). For the RCE camera 134, this may be an offset of 27.5 degrees or 320 pixels in x and 240 pixels in y. This assumption may no longer estimate the lumen center with as much accuracy as before such that the system 300 can assert a new boundary on the centeredness and expected error in estimates and attempt to use additional information within the image to make estimates. In the absence of a strong peak, the aspect ratio of these b-closed segments 914 may be used to estimate yaw and pitch angle of the camera 134. Thus, for the X-offset angle, the system 300 may use the difference of the aspect ratio $S_w/S_h$ with an assumed ideal aspect ratio of 0.5 if the segment were to be perfectly centered on the frame boundary. A weight may be applied this aspect ratio error with the segment height and subtracted from the upper centeredness bound, based on above equations (4c), (5c). This estimate makes several assumptions about the geometry of the haustral folds, including that each fold has a 1:1 aspect ratio, that the height of each fold is constant across its width (i.e., rectangular), etc. However, such assumptions may be accepted as additional noise in the measurement, and rather than attempting to more accurately model the high level of variation, weighting these estimates significantly less than the closed segments 912 when all estimates are eventually combined may be applied.

Similarly to the peakless b-closed segments 914, b-crossing segments 916 and c-crossing segments 918 (shown in panels D-E 708, 710 of FIG. 7) may not accurately predict the image center entirely on their own. However, with the additional information provided by an image intensity map, the system 300 may still make useful predictions from these segments 916, 918. In absence of complete occlusion, an intensity map is immediately useful in determining a very noisy estimate of camera 134 orientation within the lumen and can thus give a rapid estimate concerning whether the RCE 100 is facing left or right and top or bottom. This can be quickly assessed by determining the darkest region within the image. One method may accomplish this by reducing the resolution of the Gaussian filtered image 524 to 20% of full resolution and choosing the darkest pixel in this smaller image. Using this pixel position, the system 300 may determine the darkest region within the original image. If the camera is not occluded, the darkest point of the image may occur towards the lumen center and the system 300 may thus make a quick assessment of camera 134 orientation. While this information is useful in biasing orientation, estimates towards one side or the other may provide a more thorough analysis to finely determine how far off center the camera 134 is oriented. To do this, examination of the intensity disparity that occurs on either side of b-crossing segments 916 may occur. Because a b-crossing segment 916 may occur when the RCE 100 is very close to a haustra or significantly further away, the position of these segments in the image indicates little about how far off-center the RCE is located. Similarly, the system 300 may have difficulty in assesses much from the curvature of these segments, as part of any given segment may have significantly more curvature than other parts and may not provide a good indication of how far the RCE 100 is from the segment.

While the presence of multiple b-crossing segments 916 may serve to provide some of this information, the change of intensity around a segment ($I_R$-$I_L$) can be indicative of the camera 134 angle with regard to the segment and the lumen center. If, for example, the camera 134 is facing the lumen wall, the lighting provided by the LEDs 138 on the left and right of the camera) may illuminate both sides of the image equally, resulting in a relatively uniform intensity distribution across both sides of the image frame. As the camera 134 begins to turn towards the center, some of the light may travel down the lumen, resulting in a significant intensity disparity across each segment. By considering this intensity disparity, the system 300 may form a rough estimate of the orientation offset of the RCE 100 from the lumen center. Although using b-crossing segments 916 as an example here, this intensity disparity method may be applied to c-crossing segments 918 if the image is broken into quadrants rather than halves. Thus, using this intensity disparity method, the system 300 may determine a useful estimate for the center, even when no center is visible in the image frame. While these segments have the potential to appear at any camera 134 orientation due to poor segmentation, in practice these segments rarely occur when the camera has a clear view of the lumen. The system 300 thus may place an additional upper bound on the centeredness estimate of 115 pixels in the x direction or approximately 10 degrees off-center, based on evaluative testing of this method. Equations (6), (7) prescribe a simple linear equation to the intensity disparity method based on initial evaluative testing in a simulated environment.

$$X_{bcr} = \begin{cases} 10 + 40\left(0.5 - \dfrac{I_R - I_L}{255}\right), \text{ for left facing} \\ -10 - 40\left(0.5 - \dfrac{I_R - I_L}{255}\right), \text{ for right facing} \end{cases} \quad (6)$$

$$Y_{bcr} = \begin{cases} 10 + 40\left(0.5 - \dfrac{I_B - I_T}{255}\right), \text{ for top facing} \\ -10 - 40\left(0.5 - \dfrac{I_T - I_B}{255}\right), \text{ for bottom facing} \end{cases} \quad (7)$$

Open segments 920 as shown in panel F 712 of FIG. 7 can be problematic as they tend to result from a poor segmentation and thus may be inaccurate. To make use of the open segments, the system 300 may make an assumption that the images may form a closed or nearly closed curve if properly segmented. As noted previously, the system 300 may filter out any open segments with aspect ratios $A_r$, heights and widths outside of a specific threshold, as well as any segments with fewer than 6 unique extreme points, and then attempt to fit a closed curve to these segments. The system 300 may first fit an ellipse to the segment 920. However, ellipse fitting may provide a good fit for more triangulated haustra, but provide an inaccurate reconstruction (an elongated ellipse for example). If the ellipse fit is poor, or results in an ellipse of aspect ratio beyond the threshold, they system 300 may next fit a triangle to the segment 920. If this fit results in a triangle where one or more of the angles are less than 90 degrees, the system 300 may consider this to be a good fit for this open segment 920, and use the centroid of this triangle to form the center estimate. Alternatively, if the original ellipse fit is good, the system 300 uses that centroid to estimate the center. As noted, the system 300 may consider these formerly open segments 920 that have been successfully closed by shape fitting as o-closed segments.

If the segment does not fit the requirements for shape fitting or shape fitting is unsuccessful, the segment is still considered open. Because these segments typically are incomplete and have the potential to give misleading estimates, the system 300 may use the intensity disparity method previously used on b-crossing segments 916 to estimate the lumen center from these open segments 920, illustrated through equations 8a-9b below.

$$X_{op} = \begin{cases} \alpha\left(\dfrac{W}{2} - \dfrac{1}{n}\sum_{i=1}^{n} x_i\right), \text{ for 0-closed} & (8a) \\ 10 + 40\left(1 - \dfrac{I_R - I_L}{255}\right), \text{ for open} & (8b) \end{cases}$$

$$Y_{op} = \begin{cases} \beta\left(\dfrac{H}{2} - \dfrac{1}{n}\sum_{i=1}^{n} y_i\right), \text{ for 0-closed} & (9a) \\ 10 + 40\left(1 - \dfrac{I_B - I_T}{255}\right), \text{ for open} & (9b) \end{cases}$$

Once all segment estimates 926 are compiled, an overall orientation estimate may be calculated based on some combination 928 of the individual estimates. For this, the system 300 may consider the general accuracy of each of the described methods, as well as the overall size of the most accurate segment types. The presence of any closed segments 912 significantly improves the quality of the estimate and thus the weight of closed segments, when present, may be higher than any other segment. In addition, o-closed segments, while potentially less accurate than closed segments, are also trustworthy given the stringent constraints ultimately placed on them. The system 300 may thus combine closed and o-closed segment estimates for the weighting. B-closed segments 914 that have been successfully fitted to a shape or that have strong peaks may also be accurate as the lumen center is still estimated within the image itself, such that these may also be weighted at the same or similar level as the closed segments 912. In one implementation and for these more accurate segments, the system may prescribe 90% of the overall estimate weight (if some of these segments are present). In some implementations, because one goal in navigation is to identify the lumen center as close to the RCE 100 as possible (i.e., not far down the lumen), the system 300 may weigh the estimates from those segments which have the greatest overall area and are thus assumed to be the closest to the RCE with 80% of their respective weight. While the final weighting may be generally dependent on the number and existence of each segment type, this distribution ensures that, when large, accurate segments are present, they have a disproportionate weight on the lumen center position.

B-crossing 916, c-crossing 918, and open segments 920 may be the least accurate segment types. Thus, when these types of segments are present along with other more accurate segments, the system may, in some implementations, give a lower weight (such as only 10%) of the overall estimation power and, in contrast to the more accurate segments, this distribution is not size dependent. Thus, the presence of a single closed 912, b-closed 914, or o-closed segment can significantly bias the final estimate towards that curves independent estimate, however the system 300 may still be able to form useful predictions even when oriented significantly off of the lumen's center. In example overall weighting function is shown in equation (10) below. Note that each class weight, $\lambda$, may be dependent on the number of segments that occur.

$$X_{est} = \lambda_1 \left[ 0.8 * X_{cl,1} + \frac{0.2}{n_{cl}-1} \sum_{i=2}^{\eta_{cl}} X_{cl,i} \right] + \\ \lambda_2 \left[ 0.8 * X_{bcl,1} + \frac{0.2}{n_{bcl}-1} \sum_{i=2}^{\eta_{bcl}} X_{bcl,i} \right] + \\ \frac{\lambda_3}{\eta_{bcr}} \sum_{i=1}^{\eta_{bcr}} X_{bcr,i} + \frac{\lambda_1}{\eta_{op}} \sum_{i=1}^{\eta_{op}} X_{op,i} \quad (10)$$

One advantage of the method described above is that it provides the ability for the RCE 100 to navigate and/or make decisions based on its estimated orientation, even when not facing the center of the lumen. This is important for several reasons. When navigating tight turns, it is possible the device 100 may be primarily wall-facing. This system provides the ability to recognize when the device 100 is in such a state and navigate accordingly. Additionally, external disturbances, such as a tether snag, can easily result in large changes to the RCE's pose. This system provides the ability to recognize when the device 100 is no longer well-centered and to respond accordingly. Finally, endoscopy is not primarily about navigation, but rather visualization/intervention. The systems and methods discussed herein provide the ability for any robotic endoscope to seamlessly transition from visualizing the tissue to navigating to the next section of tissue that much be visualized.

Figure 10:
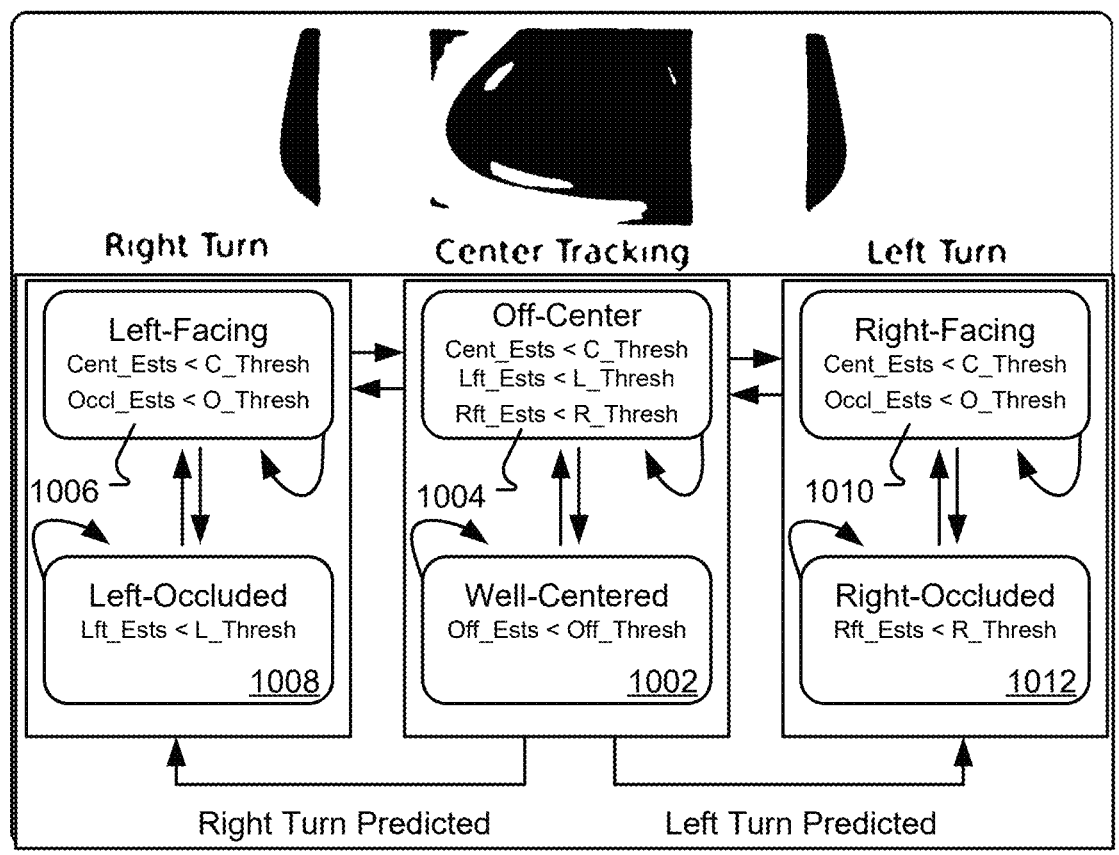
FIG. 10 is an overview of a state machine for use with the robotic capsule endoscope system.

To more effectively utilize a region estimator and to avoid the problem of spurious estimates, the system 300 may also incorporate state dependency, as shown in FIG. 10. In particular, the system 300 may break the pose estimates into six discrete regions, well-centered 1002, off-center 1004, left-wall facing 1006, left-occluded 1008, right-wall facing 1010, and right-occluded 1012. Note that the system 300 may not include any pitching states in this formulation, even though pitch in the region estimates may be included. Some RCE devices 100 may not control pitch to maneuver successfully and, thus, the system 300 may not include these estimates in the relevant navigation states, however these states may be added for use on more conventional scopes. The system 300 may define the inner four (non-occluded) states based on the estimated angle from the region estimator and based on the previous frames processed. The device 100 may begin in the well-centered state 1002 and remain in that state until the lumen center estimate error is greater than some threshold value (such as 10 degrees) for a fixed threshold of consecutive frames. Once this threshold is reached, the system 300 moves to the off-center state 1004 where it will again remain until an error and frame threshold is reached, toward either the left 1006 or right wall 1010 direction. While in some regard the state dependency of the system 300 may amount to low pass filtering of the region estimates (as the system uses multiple adjacent weighing in the same direction before a transition can be made), this state dependency also eliminates the possibility of erroneously moving between non-adjacent states (skipping from left to right for example), instead forcing the system to move between states that are adjacent to one another. Once the system 300 has entered the right-facing 1010 or left-facing 1006 state, it is possible that the camera 134 will become so close to the wall of the lumen that useful estimates may not be possible. To manage these wall occlusions, the system 300 may introduce left 1008 and right-occluded 1012 states. These states are reached if, while in the left or right-wall state, the system 300 is unable to find any useful segments for a fixed threshold of frames.

One advantage of the state-dependency of this system 300 is that it enables the implementation of multiple state-dependent controllers to better accommodate the navigational needs of an endoscopic device 100. For the purposes of robotic capsule endoscopy 100, the lumen region and center estimation method presented above provides a quick interpretation of the in vivo scene for both low level control and higher-level decision making. While lumen center tracking strategies may demonstrate success when the lumen is clearly seen, the tight turns of the GI tract may occur such clear views will not always be possible. To explore the potential to use this algorithm for control purposes, a multi-part lumen center controller is provided. This controller combines lumen center tracking with a tight curve navigation system to allow the RCE 100 to autonomously navigate straight paths, large curves, and tight curves within the colon or other body lumen. The state machine thus allows clear delineation between separate control modes and to determine when the controller transitions to each different mode.

In general, lumen center alignment of the RCE 100 aids in successful control of the RCE. The ability to become centered in the lumen enables both superior mobility (compared to rubbing against the wall, or driving directly into it) and superior visualization (enabling both better diagnostic capabilities and better estimation for future navigation goals). Lumen center tracking is thus a component of the robotic endoscope control strategy. To control lumen center position, feedback from the lumen center estimate and the region estimate from the visual estimator may be used to compute the control mode and error, using equation (11) below.

$$E = F_{center} - Est_{center} \quad (11)$$

$$\omega_r = \begin{cases} |E| * D_{PID}, & \text{for } |E| > 30 \\ \omega_{max} - E * K_P, & \text{for } 0 < E < 30 \\ \omega_{max}, & \text{for } -30 > E < 0 \\ \omega_{max}, & \text{for right facing state} \\ -\omega_{max}, & \text{for left facing state} \end{cases} \quad (12)$$

$$\omega_i = \begin{cases} |E| * D_{PID}, & \text{for } |E| > 30 \\ \omega_{max}, & \text{for } 0 < E < 30 \\ \omega_{max} - E * K_P, & \text{for } -30 > E < 0 \\ -\omega_{max}, & \text{for right facing state} \\ \omega_{max}, & \text{for left facing state} \end{cases} \quad (13)$$

For center tracking, the region estimate serves as the outer loop, moving the RCE 100 between several possible states. When the RCE 100 is already in the well-centered state 1002, the controller aligns the onboard camera 134 (and thus the heading of the RCE) with the estimated center. This may be accomplished, in one implementation, with a simple dual mode PID controller, as shown by the first three cases in equations (12) and (13). Thus, the controller primarily operates in the two centered states 1002, 1004. However, if the RCE 100 transitions into one of the left 1006 or right-wall facing 1010 states, the lumen center predictions may become significantly noisier (due to lack of closed curves and reliance on intensity disparity). Thus, rather than simply feeding back these noisy estimates, the system 300 may instead control the device 100 to stop and attempt to turn towards center until reaching the well-centered state 1002, as indicated by the last two cases in equations (12) and (13). These different modes of operation all determine how the right and left motor speeds $\omega_r$, $\omega_l$ of the RCE 100 may be set during the center tracking mode of operation.

Figure 11:
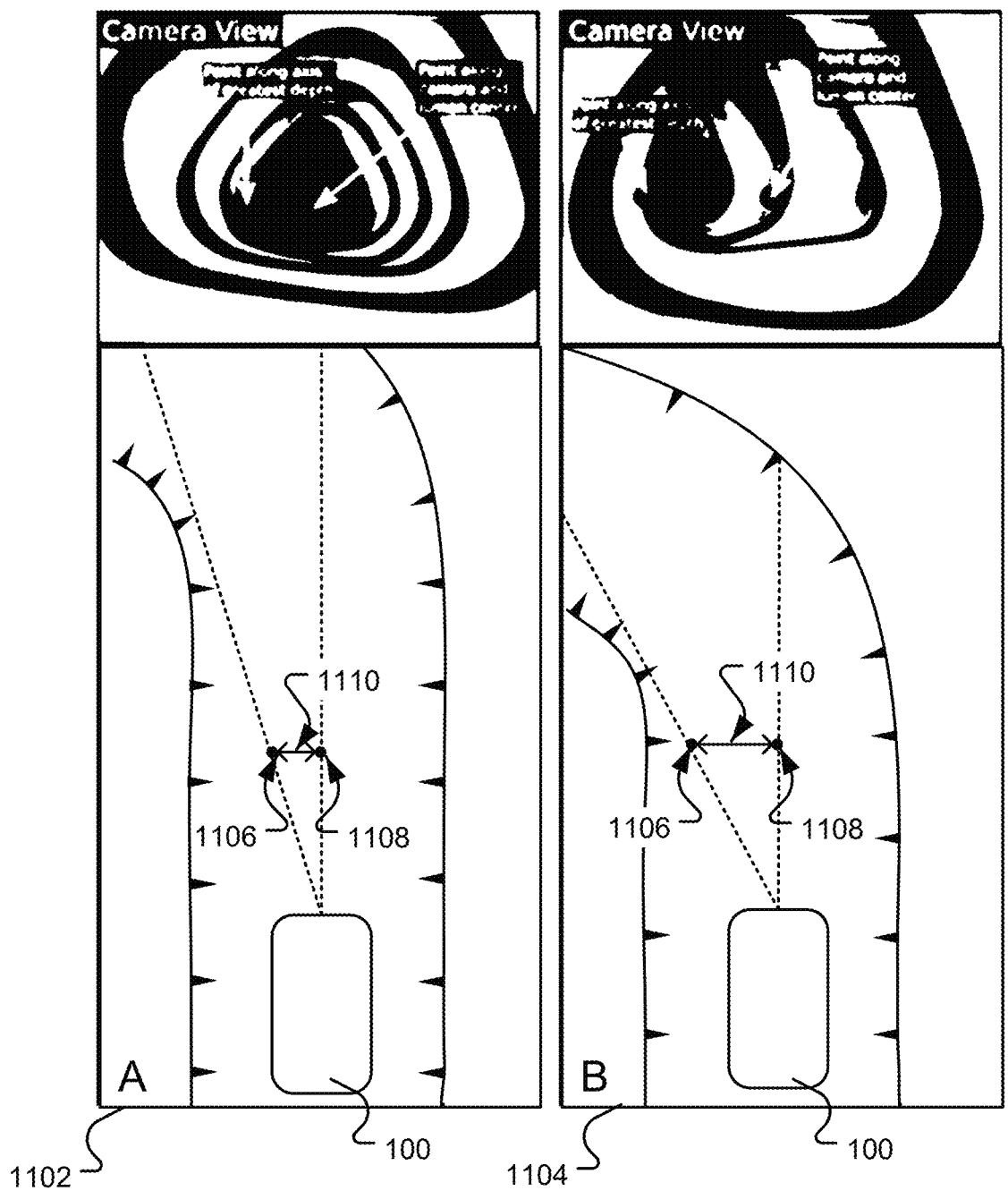
FIG. 11 illustrates a robotic capsule endoscope centering within a lumen.

Another useful component of this state-dependent architecture is that it enables the distinction of appropriate states in which to make predictions/estimates, providing greater confidence that these estimates are accurate. One application of this is in anticipating upcoming turns. While the camera 134 is in the well-centered state 1002, the expectation is that the camera has a good view of the upcoming lumen. As shown in FIG. 11, while long straight sections of the lumen (as shown in section A 1102) tend to show their darkest region $P_{dark}$ 1106 centered with the upcoming haustral folds, as the camera approaches a turn, the dark region tends to move away from the estimated center 1108 (provided by the region estimator) $Est_{cent}$ with this off-center distance 1110 increasing as the camera moves closer to the turn. Using the difference 1110 in these points, the system 300, while in the well-centered state 1002, may predict when the RCE 100 is approaching an upcoming turn. As the RCE 100 approaches a turn, the device may determine when a difference 1110 between $P_{dark}$ 1106 and $Est_{cent}$ 1108 passes a fixed pixel threshold for five consecutive frames based on equation (14):

$$\text{Turn} = \begin{cases} \text{Left}, & \text{for } Est_{cent} - P_{dark} > 110 \ px \\ \text{Right}, & \text{for } Est_{cent} - P_{dark} < -110 \ px \end{cases} \quad (14)$$

Through the equation, the controller switches to a turn anticipation mode in which it will no longer attempt to track the center, but will rather begin to steer towards the outside of the upcoming turn to create more space for the device 100 to maneuver. As shown by the arrows transitioning to the outer states in FIG. 10, the center tracking controller switches modes and imposes a temporary switch to our left or right facing state until the device has found the lumen wall (as indicated by successfully occluding the camera). This adjustment allows the controller to seamlessly switch into the tight turn control mode just before reaching the turn. This may occur because, once the device 100 has reached the beginning of the turn, it will no longer be able to reach the well-centered state 1002 and make useful predictions. In contrast to the center-tracking control mode, this is a temporary open-loop control mode of operation for the device 100, which may remain in this mode (driving slightly towards the outer wall) until it either reaches the wall-occluded state and transitions into the turn navigation control mode that follows, or transitions to the well-centered state 1002, indicating the turn prediction was incorrect. If this occurs, the device 100 may simply continue with the center-tracking control described previously.

When the RCE 100 is navigating tight turns, the length of the device, width of the lumen, and the radius of the turn may all limit the degree to which the device can face the center while still remaining mobile, and thus, mobility may be more effectively served by driving towards the outside of the turn (towards the lumen wall) and pivoting the device right before reaching the wall. These tight turns may include an alteration of the more intuitive center-tracking navigation strategy, in which rather than attempting to center the camera in the lumen, the aim becomes one of tracking the outer wall of the lumen. To accomplish this, a region estimator, along with the turn prediction mode described above, may be used to determine whether the device 100 has entered the right or left turn mode. The RCE 100 will then drive forward until occlusion occurs and may then attempt to turn left or right (dependent on the mode) until it reaches the right/left-wall state 1006, 1010. Once this occurs, the device 100 will again attempt to drive forward until reaching the right/left-occluded state 1008, 1012. This process may continue until the device 100 successfully transitions into the off-center state 1004, at which point the controller mode may switch back to the center-tracking mode 1002 of operation. If at any point the device is unable to maneuver out of the occluded state 1008, 1012 (i.e., it cannot successfully turn right or left) for a set threshold of time, the RCE 100 can automatically turn on insufflation (if enabled by the operator) for several seconds in an attempt to create more space.

The navigation architecture presented herein may be used to autonomously navigate an RCE device 100 through both a simulated, ex vivo environment, and/or in vivo environment. The RCE 100 may navigate both straight sections of the environment and sharp turns, even under significant wall-occlusion.

While the above techniques focus on mobility and locomotion of robotic endoscopes, such techniques and others may be implemented in colonoscopy intervention procedures, such as removal of a suspected polyp. In a traditional colonoscopy, the intervention is performed by an experienced endoscopist and requires precise, flexible, and fast operations of endoscopic surgical instruments. However, there are many difficulties in intervening within the colon, including lack of dexterity and unstable positioning.

As such, further provided herein is a system, device, method, technique, and the like for an autonomous colonoscopy intervention using the RCE 100, with a focus on autonomously delivering the endoscopic surgical instruments to a target polyp. The system described herein may include the RCE 100, the user interface 302, and an auto-feeding mechanism 1202 for biopsy instruments. In some implementations, a magnetically tracked sensor corresponding to the RCE 100 may be used for acquiring locations and orientations of RCE in real-time. The system can localize the target polyp 1204 and drive the instrument 100 to the polyp position autonomously.

Figure 12:
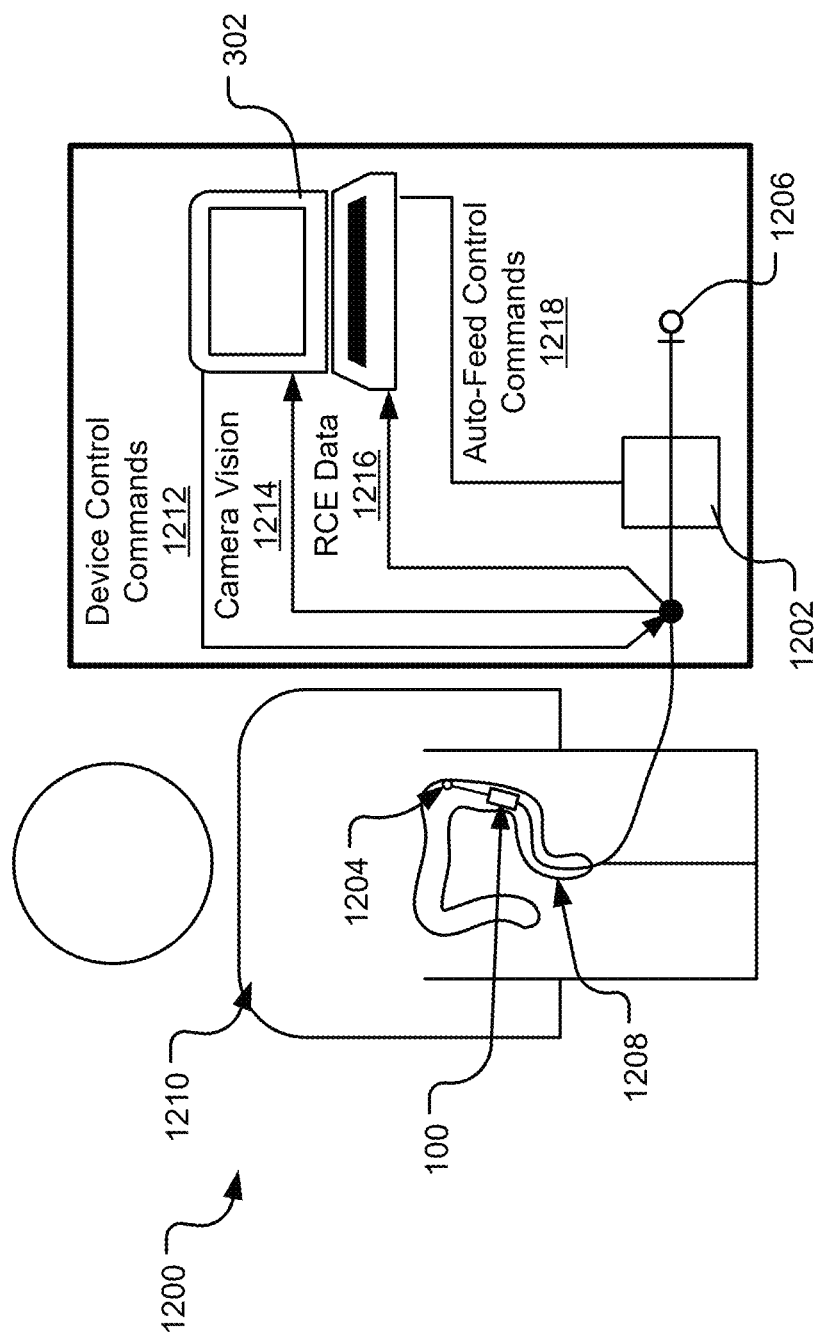
FIG. 12 illustrates an autonomous colonoscopy intervention system according to one implementation.
Figure 13:
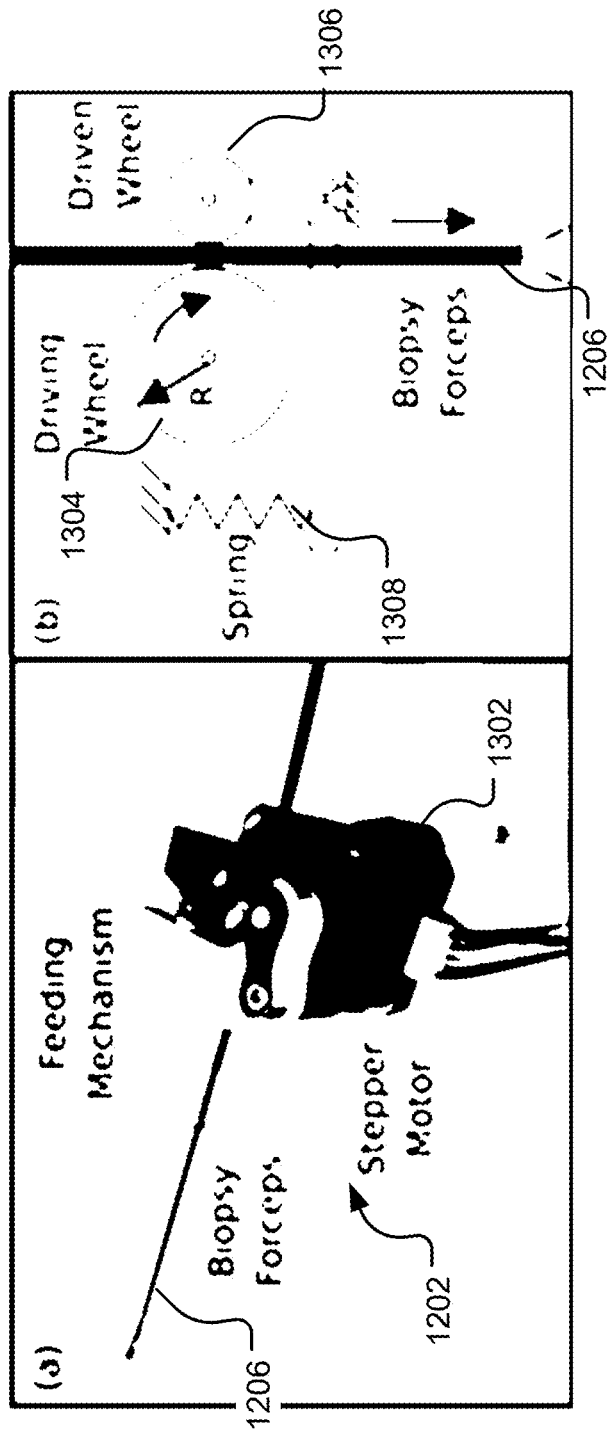
FIG. 13 illustrates an auto-feeding mechanism for biopsy forceps of an autonomous colonoscopy intervention system.

One example system 1200 for autonomous colonoscopy intervention is shown in FIG. 12. This system 1200 may include the RCE 100 described above, an auto-feeding mechanism 1202, biopsy forceps 1206, and the user interface 302. During a colonoscopy procedure, the RCE 100 may enter the gastrointestinal (GI) tract 1208 of a patient 1210 to inspect diseased polyps 1204, then extends the biopsy forceps 1206 and adjusts the device's orientation to treat the polyp. The RCE system 1200 may be useful for quickly developing and testing strategies for improving GI inspection and surgical treatment and may include the same or similar construction as described above. To improve the accuracy and automation of the whole system, the biopsy forceps 1206 may be extended automatically by the auto-feeding mechanism 1202. The auto-feeding mechanism 1202 used by the RCE 100 can transfer the biopsy forceps 1206 forward, while the displacement and velocity are controlled by a stepper motor 1302 (as shown in FIG. 13) integrated into the auto-feeding mechanism. As also shown in FIG. 13, the auto-feeding mechanism 1202 may include of a driving wheel 1304 in mechanical communication with the stepper motor 1302, a driven wheel 1304, and a tensioning spring 1308. The driving wheel 1304 is actuated by the stepper motor 1302, while the driven wheel 1306 is forced against the biopsy forceps by the spring 1308 so that the forceps 1206 can move forward with the rotation of the driving wheel. The spring 1308 exerts pressure on a link that connects the driven wheel 1306 with the driving wheel 1304. The auto-feeding mechanism 1202 may be adapted to endoscopy instruments of varying sizes. For the biopsy forceps 1206 used in this system, there is little to no noticeable slippage during transmission, thus the displacement of the endoscopy instrument can be calculated as I=2nπR, in which R is the radius of the driving wheel, and n is the number of motor revolutions.

FIG. 12 illustrates some of the devices outside the patient 1210, including the user interface 302 and the auto-feeding mechanism 1202. The user interface 302, in one implementation, may transmit control commands 1212 to the RCE 100 and auto-feed control commands 1218 to the auto-feeding mechanism 1202. In one implementation, the motor control commands 1212 for setting wheel direction/speed for the RCE 100 may be sent wirelessly, while the stepper motor control commands 1218 for the auto-feeding mechanism 1202 may be sent by USB serial connection. A magnetic tracking sensor may be attached to RCE 100 to measure a 6 degrees of freedom pose including global position (X, Y, Z) and orientation (pitch, roll, yaw) of the device. This pose data 1216 may also sent to the user interface 302. A long flexible tube is located between the auto-feeding mechanism 1202 and the RCE 100 for transferring the biopsy forceps 1206. As both the tube and the wires for signal transmission are compliant and flexible, the work platform can be moved without hindrance from its attachments.

In colonoscopy intervention, the end position of the biopsy forceps 1206 may be known in real-time, such that it can successfully extend to the polyp 1204. The collection of all possible end positions of the biopsy forceps 1206 represents the reachable workspace of this system and may depend on both the pose of the RCE 100 and the extension length of the biopsy forceps. Therefore, the modeling of the workspace for predicting the end position of the biopsy forceps is shown here.

Figure 14:
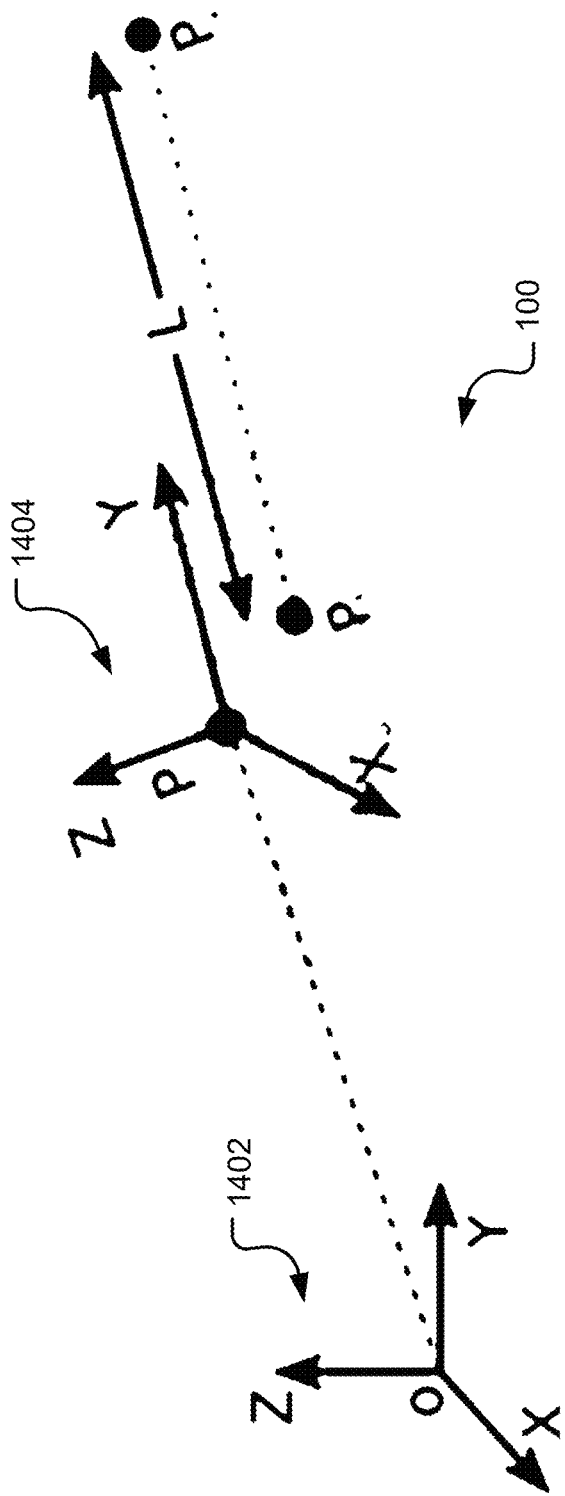
FIG. 14 illustrates a workspace analysis of an autonomous colonoscopy intervention system.

To describe the end position of biopsy forceps 1206, a world coordinate system may be defined as the center of the magnetic source of the magnetic tracking system of the RCE 100. As shown in FIG. 14, X-Y-Z defines the world coordinate system 1402, and $X_0$-$Y_0$-$Z_0$ is used to describe the local RCE coordinate system 1404. $P_0$ is the measuring point of the magnetic sensor which is used to measure the pose of the RCE 100 and may also be the origin of the RCE coordinate system 1404. $P_1$ is the section center of the biopsy forceps 1206 at the front end of the RCE 100, and $P_2$ is the end of biopsy forceps. L is the extended length of biopsy forceps 1206 from the front of the RCE 100 and along the direction of $Y_0$ in the RCE coordinate system 1404. For simplification, the initial RCE coordinate system 1404 is parallel to the world coordinate system 1402, in which X, Y, Z axes have the same directions as that of $X_0$, $Y_0$, $Z_0$ axis. This is achieved by adjusting the initial pose of the RCE 100 to make the two coordinate systems parallel, and then zeroing out the orientation of the sensor. In this case, the pose of the RCE 100 can be calculated by its movement transformation matrix. According to the orientations of the RCE coordinate system 1404, $P_2$ in the world coordinate system can be calculated by (15):

$$P_2 = R_{\psi,Z} R_{\theta,Y} R_{\varphi,X}(P_1^0 + [0\ L\ 0]^T) + P_0 \quad (15)$$

In which ψ, θ, φ are the Euler angles of RCE coordinate frame with respect to world coordinate frame, $R_{\psi,Z}$, $R_{\theta,Y}$, $R_{\varphi,X}$ are the corresponding rotation matrices. $P_1^0$ is the position vector of $P_1$ relative to $P_0$ in the RCE coordinate system.

In equation (15), the extension of biopsy forceps 1206 is considered as a straight line that is parallel to the RCE 100 with a length of L. However, due to its own weight, a gradually increasing deflection occurs with the extension of the biopsy forceps 1206. Therefore, the deflection may be considered in the workspace model. As the deflection phenomenon is similar to cantilever beam deflection, a formula similar to the cantilever beam deflection model may be used to fit the deflection of the biopsy forceps 1206. The relationship between the deflection and extension length of biopsy forceps is then modeled as equation (16):

$$y_d = 1.147 \times 10^{-8} L^4 (mm) \quad (16)$$

Figure 15:
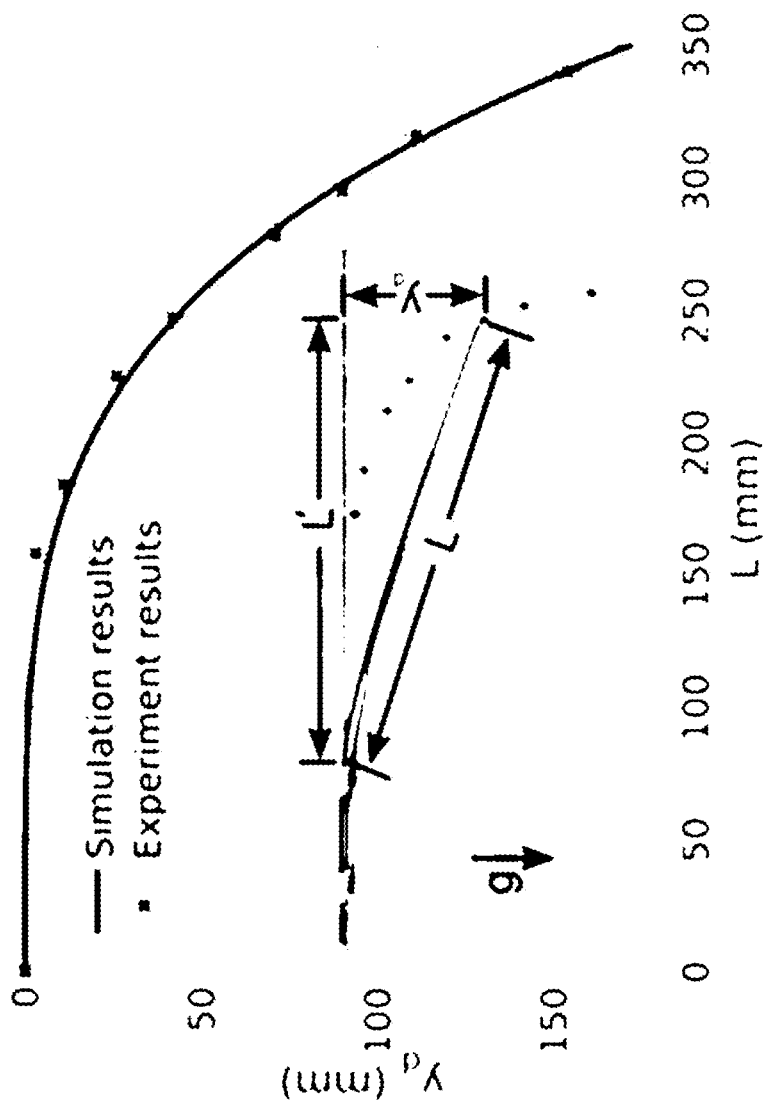
FIG. 15 illustrates a comparison of the experiment results and the simulation results of biopsy forceps deflection.

The comparison of experimental results and model simulated results of biopsy forceps 1206 deflection is shown in FIG. 15, the gravity direction is vertically downward. The model shows a good match to the measured deflection, with an R-square value of 0.9973, and an RMSE of 2.6 mm. The L' in FIG. 5 can be approximately calculated by equation (17).

$$L' = (L^2 - y_d^2)^{1/2} \quad (17)$$

Substituting (17) and (16) into (15), the end position of biopsy forceps $P_2$ can be calculated by (18).

$$P_2 = R_{\psi,Z} R_{\theta,Y} R_{\varphi,X}(R_{-\theta,Y}[0\ L'\ y_d]^T + P_1^0) + P_0 \quad (18)$$

Note that the forceps' deflection is generated in the direction of gravity. When the RCE 100 rotates along the $Y_0$ axis at an angle of θ, the bending forceps may no longer be parallel to the $X_0Y_0$-plane. In this condition the coordinates of the biopsy forceps' end can be calculated as $R_{-\theta,Y}*[0\ L'\ y_d]$.

As the biopsy forceps 1206 may be extended and retracted in a forward and back direction, the RCE 100 may move to a position with suitable posture such that the biopsy forceps can be extended to reach the target polyp 1204. Using the workspace model, a real-time end position of the biopsy forceps 1206 can be predicted. To determine whether the biopsy forceps 1206 can reach the target tissue in its current posture, the position of the target polyp 1204 may be determined. An image-based estimation of the polyp position may thus be executed.

Figure 16:
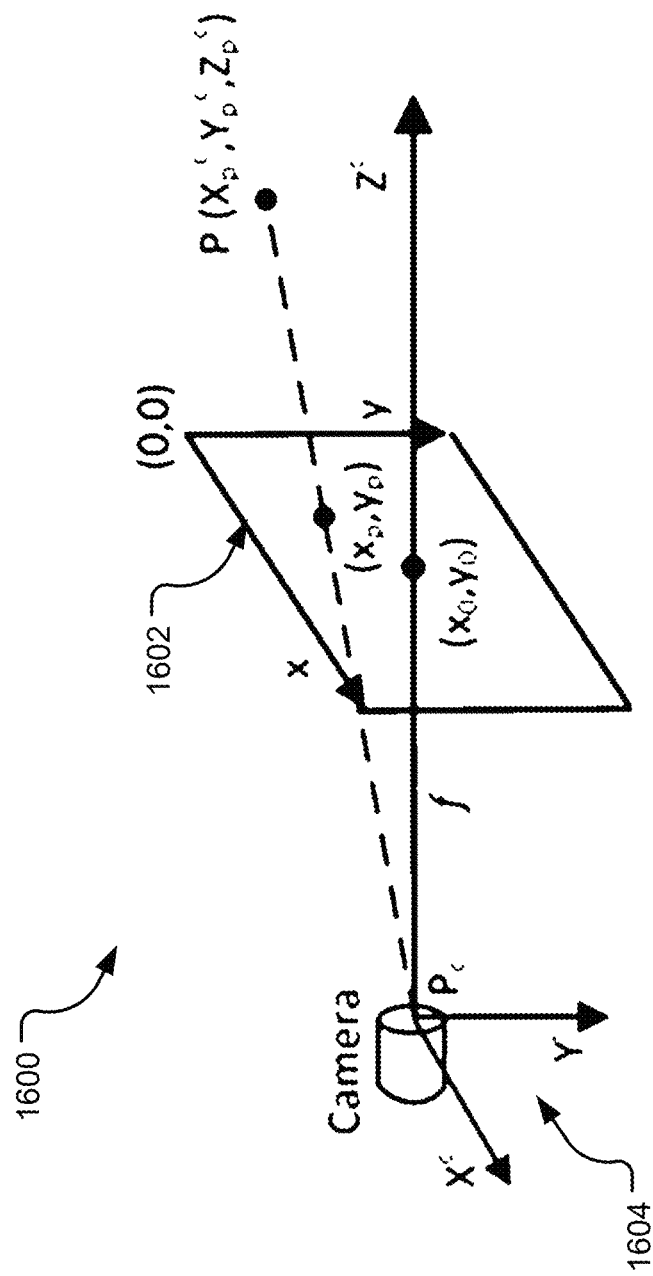
FIG. 16 illustrates a pinhole camera model for use with an autonomous colonoscopy intervention system.

FIG. 16 shows a pinhole camera model 1600, where $X^c$-$Y^c$-$Z^c$ is the camera coordinate system 1604, the image plane x-y is the camera projection plane 1602. $P_c$ is the origin of the camera coordinate system 1604, the physical distance between $P_c$ and the image plane 1602 is the focal length f. P is a random point in 3D space, $(X_p, Y_p)$ is the projection of P on the image plane 1602 that expressed as pixel coordinates, and $(X_0, Y_0)$ is the pixel coordinates of the camera center in the image plane. The coordinates of P in the camera coordinate system can be calculated by the following equation.

$$\begin{bmatrix} X_p^c \\ Y_p^c \\ Z_p^c \end{bmatrix} = Z_p^c \begin{bmatrix} (x_p - x_0)/f \\ (y_p - y_0)/f \\ 1 \end{bmatrix} \quad (19)$$

Considering the coordinate system transformation from the camera coordinate system 1604 to the world coordinate system 1402 shown in FIG. 4, the coordinates of point P in world coordinate system can be expressed as (6), in which $[X_p^c Z_p^c -Y_p^c]$ is the rotated coordinates of point P from the camera coordinate system to RCE coordinate system 1404.

$$\begin{bmatrix} X_p \\ Y_p \\ Z_p \end{bmatrix} = R_{\psi,Z} R_{\theta,Y} R_{\varphi,X} \left( \begin{bmatrix} X_p^c \\ Z_p^c \\ -Y_p^c \end{bmatrix} + P_c^0 \right) + P_0 \quad (20)$$

Here, $P_c^0$ is the position vector of $P_c$ relative to $P_0$ in the initial RCE pose in the world coordinate system.

As there may only be a single camera 134 on the RCE 100, determining the absolute depth of the target point P may be difficult, as referred to as $Z_p^c$ in equation (20). In this condition, for a single set of the measured data including magnetic sensor measurement data and the pixel coordinates of the target point in a recorded image, an estimated straight line that passes through P and $P_c$ is provided. Theoretically, to determine the coordinates of the target point, at least two such estimated lines may be used such that their point of intersection can be determined. However, in practical applications, the two estimated lines may be unlikely to intersect in 3D space due to measurement errors, therefore an optimal position of the target point may be calculated instead. To further improve the estimation accuracy, multiple views may be used for estimating the position of the target point.

With the workspace model and position model for the polyp 1204 determined, the system may estimate the positions of the biopsy forceps 1206 end and the polyp. On this basis, the system may carry out the autonomous colonoscopy intervention as follows. First, when the RCE 100 drives near a suspected polyp 1204 (as observed via real-time camera feedback 1214), the RCE may be stopped to provide a good view of the polyp. The user or computing device may select the tracking area on the suspected polyp 1204 for colonoscopy intervention by tracing a bounding box around the polyp within the user interface 302. In some instances, this may be the only step in the autonomous colonoscopy intervention that utilizes manual operation by the physician who may decide which areas or polyps require interventions. The remainder of the process may be automatically completed by the robotic system. Once the polyp area 1204 has been selected, the RCE 100 may automatically take several views of the selected area in different positions and orientations. Once these images have been captured, the system estimates the position of the centroid of this area from both the captured views 1214 and the measured RCE pose data 1216. According to the estimated polyp 1204 position, the RCE 100 autonomously adjusts a pose to extend the biopsy forceps 1206 for colonoscopy intervention. Thus, this process may include two autonomous driving procedures. The first one is to take different views of the polyp 1204 for reconstructing its 3D position in the world coordinate system 1402. The second procedure adjusts the RCE's location and orientation such that the extended biopsy forceps 1206 can reach the target polyp.

Figure 17:
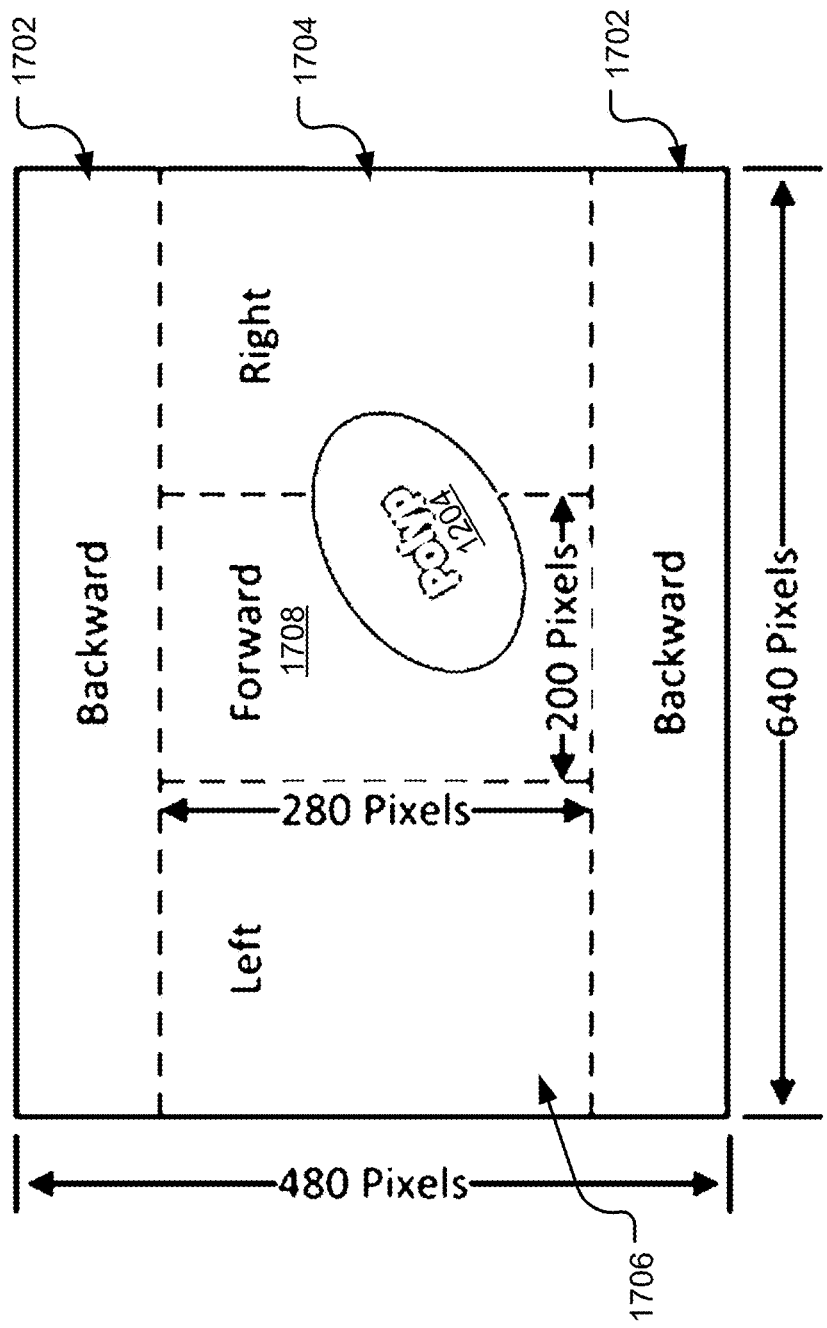
FIG. 17 illustrates an autonomous driving strategy of an autonomous colonoscopy intervention system for tracking polyp and recording multiple views.

One autonomous driving strategy of the RCE 100 for recording multiple views of the polyp 1204 is shown in FIG. 17. In one instance, the size of a single view is 640×480 (pixels), and each view may be divided into 5 regions, where the size of the central region is 200×280 pixels. The regions in the top and bottom are Backward regions 1702, the left and right regions are defined as Left 1706 and Right 1704 regions respectively, and the central region is the Forward region 1708. The name of each region corresponds to the command of the RCE motion, and the priority of the four commands follows a descending order of Backward, Left, Right, and Forward. For example, as FIG. 17 shows, the polyp 1204 occupies two regions (Forward 1708 and Right 1704), as the Right command has priority over the Forward command, the RCE 100 may first receive a Right command and begin turning right followed by the Forward command for the next motion. In the first frame of view, the polyp 1204 should be fully present. This is applicable in practice because the RCE 100 can be stopped when the polyp 1204 is fully observed, followed by selecting the tracking area via a bounding box on the polyp in the first view. The RCE 100 may follow these commands to continue moving and tracking the polyp 1204 and may then extract any number of views (at equal time intervals), from the recorded views. Of these commands, the Backwards may be the highest priority command because it captures a larger range of the scene; under this circumstance, the tracking loss can be significantly avoided. Further, if the backward region 1702 is relatively narrow, the polyp 1204 may be easily seen in the middle regions so that the RCE 100 is less likely to travel far from the polyp. In this case, the estimation error on the polyp position caused by the significant distance between the RCE 100 and the polyp 1204 can be largely avoided. The Forward region 1708 may be relatively small because the RCE 100 may be encouraged to take views in different orientations to provide a larger baseline between views and thus a more accurately estimated 3D location of the polyp. There is no fixed order for the priority of Left and Right commands, which means the priority order of the two commands can be reversed.

Figure 18:
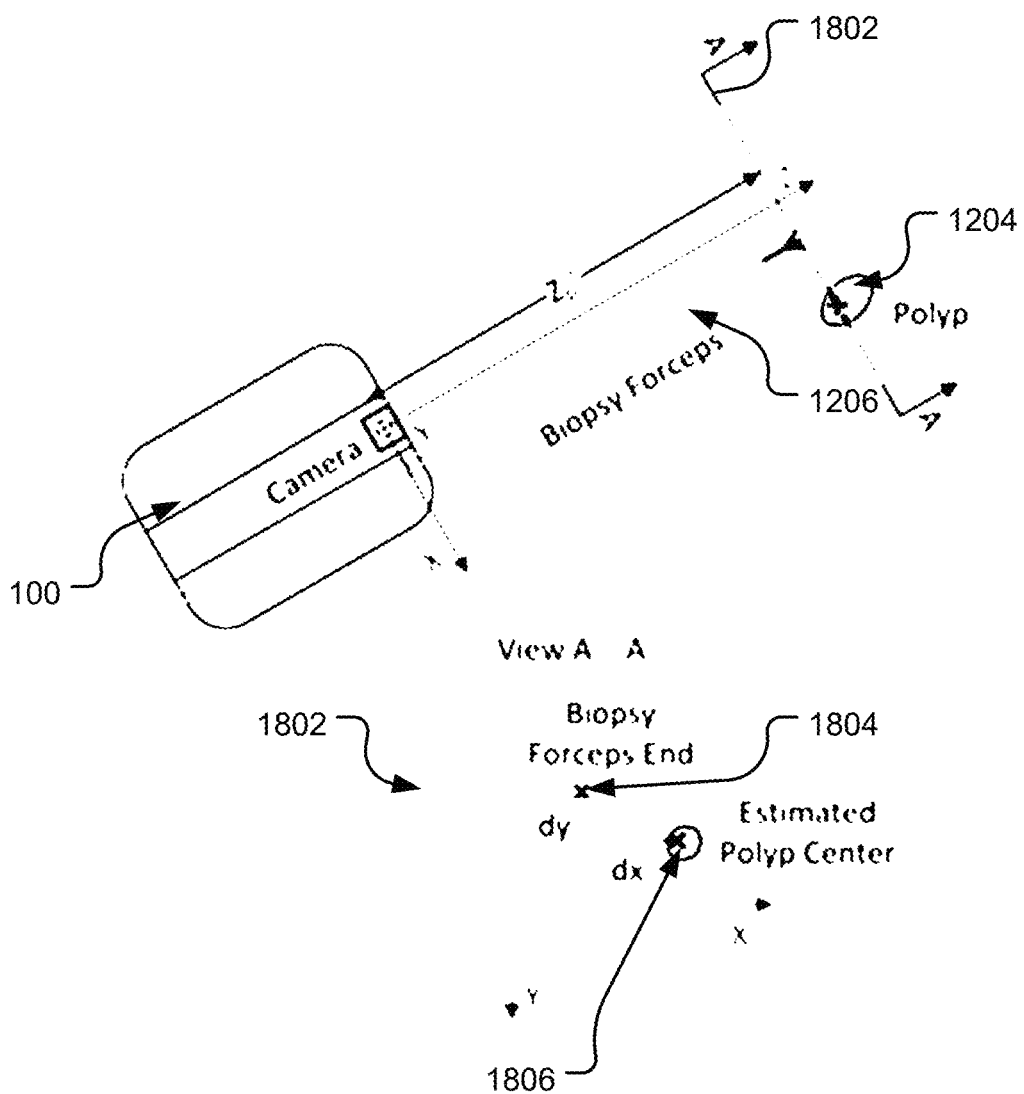
FIG. 18 illustrates an autonomous pose adjustment for an autonomous colonoscopy intervention system.

The second mode of autonomous driving for the RCE 100 may be an adjustment to its location and orientation according to the estimated polyp position. The control strategy for autonomous pose adjustment is explained in FIG. 18. The camera 134 and biopsy forceps 1206 have the same orientation as that of RCE 100, and thus for simplicity, they may be considered within the camera coordinate system. In FIG. 18, the $Z^c$-axis coordinate of the estimated polyp 1204 in the camera coordinate system is $Z_p^c$. The coordinates of the end of biopsy forceps 1206 with a $Z^c$-axis coordinate of $Z_p^c$ can be estimated by the workspace model. View A-A 1802 is the view plane that contains the estimated polyp position and is perpendicular to the $Z^c$ axis. As View A-A 1802 shows, the first x-marker 1804 is the end position of biopsy forceps, the green x-marker 1806 is the estimated polyp position. dx and dy are the position differences between the two crosses in $X^c$ axis and $Y^c$ axis respectively, which are defined as the difference between the biopsy forceps end 1804 and polyp center 1806.

To adjust its pose for colonoscopy intervention, the RCE 100 will turn left or right to reduce the absolute value of dx within an error tolerance $x_{err}$. The RCE 100 will then move forward or backward to reduce the absolute value of dy to within an error tolerance $y_{err}$. The haustral folds in the colon lumen can affect the pitch angle of the RCE, as a result, the $Y^c$ coordinate of the end of biopsy forceps 1804 can be changed. However, it is difficult to control this unknown environmental factor, therefore the system may use of the deflection of the biopsy forceps 1206 to adjust the end position of these forceps in the $Y^c$ direction instead. If dy>0, which indicates the end of the biopsy forceps 1804 is higher than the polyp center 1806, the RCE 100 will move backward and $Z_p^c$ will increases such that the deflection of the biopsy forceps will increase to reduce the absolute value of dy. In contrast, if dy<0, the RCE 100 will move forward to reduce the deflection of the biopsy forceps thereby reducing the absolute value of dy. Once both dx and dy are within the error tolerances, the RCE 100 will stop, and the current posture of RCE is considered to be a suitable posture for colonoscopy intervention. The auto-feeding mechanism 1202 may next transmit the biopsy forceps 1206 to the position of the polyp 1204. When the end of the biopsy forceps is placed at the inlet of the long tube connected to the auto-feeding mechanism 1202, the feeding length of biopsy forceps is the sum of the tube's length and extension of the biopsy forceps, in which the extended length of biopsy forceps can be calculated according to equation (16) with the known deflection.

With the proposed control strategy for autonomous colonoscopy intervention, an estimation and control strategy for autonomous colonoscopy intervention on the RCE 100 is presented. Standard surgical tools can be used by the RCE 100 and can be delivered robotically by the auto-feeding mechanism 1202. The biopsy forceps 1206 are used as an example in this disclosure, but other surgical tools can also be used after building their deflection models. The end position of the biopsy forceps 1206 is predicted by the workspace model, and the location of the target polyp center 1804 is estimated using the polyp position model. Both the RCE motion control for tracking and capturing multiple views of the polyp 1204 and the RCE pose adjustment control for colonoscopy intervention are proposed. With this strategy, the RCE 100 can autonomously calculate the position of the polyp 1204, adjust its posture, and deliver a standard surgical tool to the polyp for intervention. The autonomous colonoscopy intervention experiments on a half colon simulator, a closed colon simulator and the simulation with haustral folds, demonstrate fast operation and good accuracy using this strategy.

Figure 19:
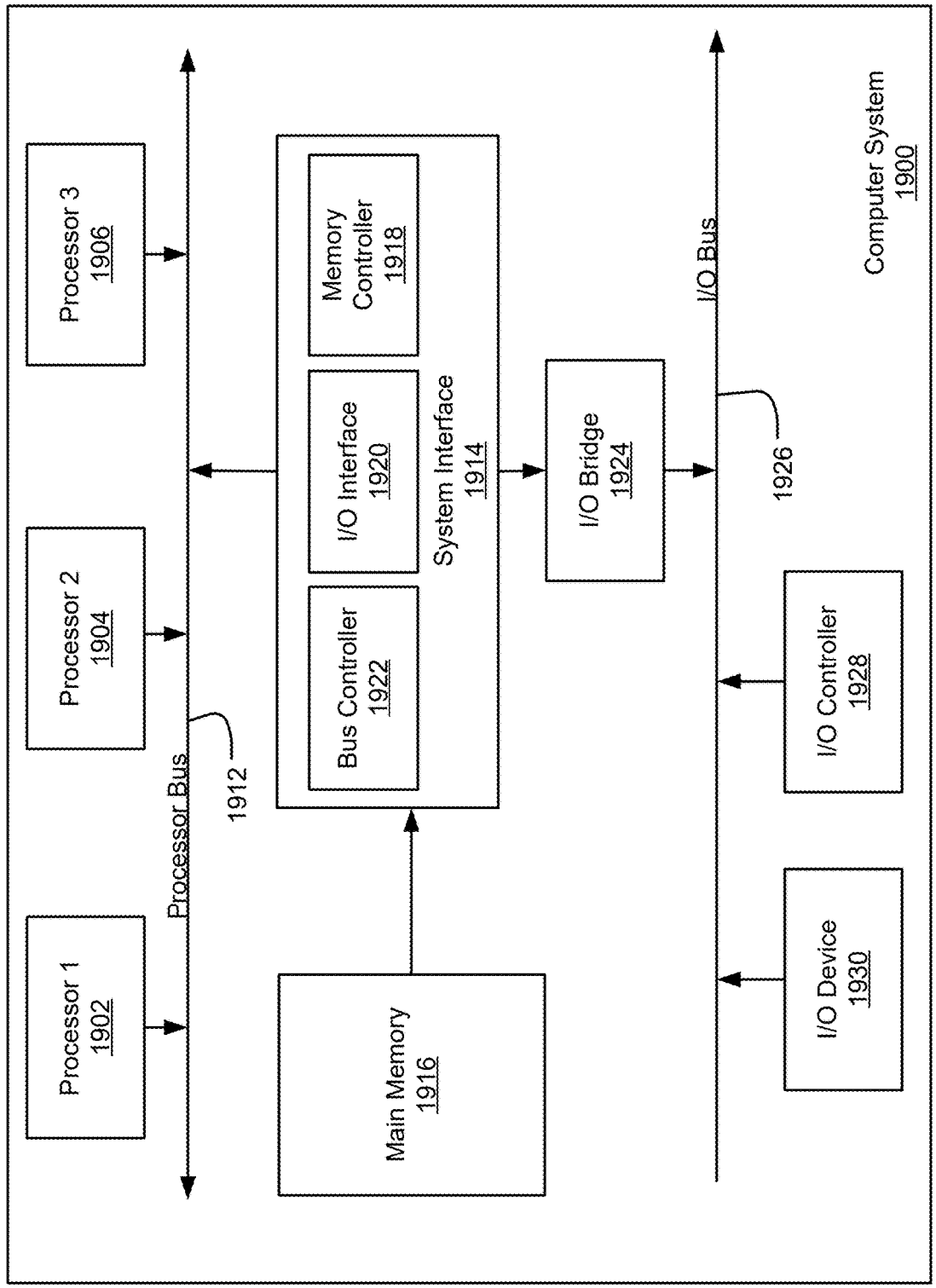
FIG. 19 is a diagram illustrating an example of a computing system which may be used in implementing embodiments of the present disclosure.

FIG. 19 is a block diagram illustrating an example of such a computing device 1900 which may be used in controlling the embodiments of the device 100 discussed herein. The computer system (system) includes one or more processors 1902-1906. Processors 1902-1906 may include one or more internal levels of cache (not shown) and a bus controller or bus interface unit to direct interaction with the processor bus 1912. Processor bus 1912, also known as the host bus or the front side bus, may be used to couple the processors 1902-1906 with the system interface 1914. System interface 1914 may be connected to the processor bus 1912 to interface other components of the system 1900 with the processor bus 1912. For example, system interface 1914 may include a memory controller 1918 for interfacing a main memory 1916 with the processor bus 1912. The main memory 1916 typically includes one or more memory cards and a control circuit (not shown). System interface 1914 may also include an input/output (I/O) interface 1920 to interface one or more I/O bridges or I/O devices with the processor bus 1912. One or more I/O controllers and/or I/O devices may be connected with the I/O bus 1926, such as I/O controller 1928 and I/O device 1930, as illustrated.

I/O device 1930 may also include an input device (not shown), such as an alphanumeric input device, including alphanumeric and other keys for communicating information and/or command selections to the processors 1902-1906. Another type of user input device includes cursor control, such as a mouse, a trackball, or cursor direction keys for communicating direction information and command selections to the processors 1902-1906 and for controlling cursor movement on the display device.

System 1900 may include a dynamic storage device, referred to as main memory 1916, or a random access memory (RAM) or other computer-readable devices coupled to the processor bus 1912 for storing information and instructions to be executed by the processors 1902-1906. Main memory 1916 also may be used for storing temporary variables or other intermediate information during execution of instructions by the processors 1902-1906. System 1900 may include a read only memory (ROM) and/or other static storage device coupled to the processor bus 1912 for storing static information and instructions for the processors 1902-1906. The system set forth in FIG. 19 is but one possible example of a computer system that may employ or be configured in accordance with aspects of the present disclosure.

According to one embodiment, the above control signals may be generated by computer system 1900 in response to processor 1904 executing one or more sequences of one or more instructions contained in main memory 1916. These instructions may be read into main memory 1916 from another machine-readable medium, such as a storage device. Execution of the sequences of instructions contained in main memory 1916 may cause processors 1902-1906 to perform the process steps described herein. In alternative embodiments, circuitry may be used in place of or in combination with the software instructions. Thus, embodiments of the present disclosure may include both hardware and software components.

A machine-readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 606 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 816, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

Various embodiments of the disclosure are discussed in detail above. While specific implementations are discussed, it should be understood this is done for illustration purposes only. A person skilled in the relevant art will recognize that other components and configurations may be used without parting from the spirit and scope of the disclosure. Thus, the preceding description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

What is claimed is:

1. An autonomous endoscope system comprising: a robotic endoscope device comprising a video camera, a microcontroller transmitting a control signal to control a movement of the robotic endoscope device; and
   a navigation computing device, in response to receiving image data of a lumen from the video camera, to:
   segment the image data by reducing the image data to a plurality of skeletonized segments of a predetermined pixel width, the skeletonized segments depicting an edge surrounding an interior surface of the lumen;
   classify the segments of the segmented image data, the classification of the segments of the segmented image data corresponding to the skeletonized segments being one of a closed segment indicating an entirety of the edge is illustrated in the segmented image data, a segment intersecting with one or more of the edges of a frame of the image data indicating at least a portion of the edge extends beyond the one or more of the edges of the frame of the segmented image data, or an open segment indicating at least a portion of the edge is missing from the segmented image data;
   estimate, based on the classification of the segments, a center point within the segmented image data corresponding to an estimated center of a lumen within the image data; and
   instruct the microcontroller to control the robotic endoscope device based on the estimated center point within the segmented image data.

2. The autonomous endoscope system of claim 1, further comprising:
   an input device in communication with the navigation computing device, the input device transmitting a control instruction to the microcontroller.

3. The autonomous endoscope system of claim 1 wherein the segmented image data is classified as at least one of the closed segment, a boundary closed segment, a boundary crossing segment, or the open segment.

4. The autonomous endoscope system of claim 1 wherein estimating the center point is based on a classification of the segmented image data.

5. The autonomous endoscope system of claim 1 wherein the navigation computing device is further to:
   combine a plurality of segmented image data by associating a weighted value to each of the plurality of segmented image data.

6. The autonomous endoscope system of claim 1 wherein instructing the microcontroller to control the robotic endoscope device comprises obtaining one or more control instructions from a state machine associated with a position of the robotic endoscope device.

* * * * *